US012186070B2

(12) United States Patent
Misener et al.

(10) Patent No.: US 12,186,070 B2
(45) Date of Patent: Jan. 7, 2025

(54) SYSTEMIZED AND METHOD FOR OPTIMIZED MEDICAL COMPONENT INSERTION MONITORING AND IMAGING ENHANCEMENT

(71) Applicant: Bard Access Systems, Inc., Salt Lake City, UT (US)

(72) Inventors: Anthony K. Misener, Bountiful, UT (US); Steffan Sowards, Salt Lake City, UT (US); Shayne Messerly, Kaysville, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/393,283

(22) Filed: Aug. 3, 2021

(65) Prior Publication Data
US 2022/0039685 A1      Feb. 10, 2022

Related U.S. Application Data

(60) Provisional application No. 63/061,120, filed on Aug. 4, 2020.

(51) Int. Cl.
*A61B 5/00* (2006.01)
*A61B 5/06* (2006.01)
(Continued)

(52) U.S. Cl.
CPC ............ *A61B 5/065* (2013.01); *A61B 5/6848* (2013.01); *A61B 5/7264* (2013.01); *A61B 5/74* (2013.01); *A61B 5/7405* (2013.01); *A61B 8/0841* (2013.01)

(58) Field of Classification Search
CPC ...... A61B 5/065; A61B 5/6848; A61B 5/7264; A61B 5/74; A61B 5/7405; A61B 8/0841
See application file for complete search history.

(56) References Cited

U.S. PATENT DOCUMENTS 4,311,138 A * 1/1982 Sugarman ......... A61M 25/0606
                                                        604/21
4,971,068 A * 11/1990 Sahi ................. A61B 5/150389
                                                        604/116
(Continued)

FOREIGN PATENT DOCUMENTS

AU        2006201646 A1     11/2006
CN         114129137 B       9/2022
(Continued)

OTHER PUBLICATIONS

PCT/US2021/050973 filed Sep. 17, 2021 International Search Report and Written Opinion dated Nov. 7, 2022.
(Continued)

*Primary Examiner* — Amal Aly Farag
(74) *Attorney, Agent, or Firm* — Rutan & Tucker LLP

(57) ABSTRACT

According to one embodiment, a guidance system is described for assisting in an advancement of a medical component within a body of a patient. The guidance system features a probe and a console. The console is communicatively coupled to the probe and features AI-based visualization controls and AI-based guidance assistance logic. The AI-based visualization controls are configured to generate, position, and reposition a visualization area between the medical component and a targeted vasculature of the patient. The visualization area is a sub-region of a total imaging area rendered by the console. The AI-based guidance assistance logic is configured to monitor for a presence of the medical component within the visualization area, provide a feedback for generating a notification that the medical component is (Continued)

within the visualization area, and apply an imaging enhancement to at least a portion of imaged data within the visualization area to assist in the advancement.

21 Claims, 12 Drawing Sheets

(51) Int. Cl.
*A61B 5/08* (2006.01)
*A61B 8/08* (2006.01)

(56) References Cited

U.S. PATENT DOCUMENTS

| | | | |
|---|---|---|---|
| 5,148,809 A | 9/1992 | Biegeleisen-Knight et al. |
| 5,181,513 A | 1/1993 | Touboul et al. |
| 5,325,293 A | 6/1994 | Dorne |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,050,523 B2 | 11/2011 | Younge et al. |
| 8,060,181 B2 | 11/2011 | Rodriguez Ponce et al. |
| 8,068,581 B2 | 11/2011 | Boese et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,155,517 B2 | 10/2015 | Dunbar et al. |
| 9,204,858 B2 | 12/2015 | Pelissier et al. |
| 9,220,477 B2 | 12/2015 | Urabe et al. |
| 9,257,220 B2 | 2/2016 | Nicholls et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,459,087 B2 | 10/2016 | Dunbar et al. |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,597,008 B2 | 3/2017 | Henkel et al. |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,380,919 B2 | 8/2019 | Savitsky et al. |
| 10,380,920 B2 | 8/2019 | Savitsky et al. |
| 10,424,225 B2 | 9/2019 | Nataneli et al. |
| 10,434,278 B2 | 10/2019 | Dunbar et al. |
| 10,449,330 B2 | 10/2019 | Newman et al. |
| 10,524,691 B2 | 1/2020 | Newman et al. |
| 10,674,935 B2 | 6/2020 | Henkel et al. |
| 10,751,509 B2 | 8/2020 | Misener |

(56) References Cited

U.S. PATENT DOCUMENTS

| | | |
|---|---|---|
| 10,758,155 B2 | 9/2020 | Henkel et al. |
| 10,765,343 B2 | 9/2020 | Henkel et al. |
| 10,896,628 B2 | 1/2021 | Savitsky et al. |
| 11,062,624 B2 | 7/2021 | Savitsky et al. |
| 11,120,709 B2 | 9/2021 | Savitsky et al. |
| 11,311,269 B2 | 4/2022 | Dunbar et al. |
| 11,315,439 B2 | 4/2022 | Savitsky et al. |
| 11,600,201 B1 | 3/2023 | Savitsky et al. |
| 2002/0038088 A1 | 3/2002 | Imran et al. |
| 2002/0148277 A1 | 10/2002 | Umeda |
| 2003/0047126 A1 | 3/2003 | Tomaschko |
| 2003/0060714 A1 | 3/2003 | Henderson et al. |
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childers et al. |
| 2006/0015039 A1 | 1/2006 | Cassidy et al. |
| 2006/0020204 A1* | 1/2006 | Serra ............... G01S 7/5208 600/437 |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0020926 A1 | 1/2010 | Boese et al. |
| 2010/0106015 A1 | 4/2010 | Norris |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0166451 A1* | 7/2011 | Blaivas ............... A61B 8/467 600/439 |
| 2011/0288405 A1* | 11/2011 | Razavi ............... G01L 1/246 600/424 |
| 2011/0295108 A1 | 12/2011 | Cox et al. |
| 2011/0313293 A1 | 12/2011 | Lindekugel et al. |
| 2012/0136242 A1* | 5/2012 | Qi ............... A61B 8/5223 604/95.01 |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1* | 4/2013 | Southard ............... C08G 61/125 600/424 |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0324840 A1* | 12/2013 | Zhongping ............... A61B 5/742 600/424 |
| 2014/0005530 A1 | 1/2014 | Liu et al. |
| 2014/0031690 A1 | 1/2014 | Toji et al. |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0257104 A1 | 9/2014 | Dunbar et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209526 A1 | 7/2015 | Matsubara et al. |
| 2015/0294497 A1* | 10/2015 | Ng ............... A61B 8/5246 382/128 |
| 2015/0297097 A1 | 10/2015 | Matsubara et al. |
| 2015/0327841 A1 | 11/2015 | Banjanin et al. |
| 2015/0359991 A1* | 12/2015 | Dunbar ............... A61B 8/4254 600/424 |
| 2016/0029995 A1 | 2/2016 | Navratil et al. |
| 2016/0029998 A1 | 2/2016 | Brister et al. |
| 2016/0058420 A1 | 3/2016 | Cinthio et al. |
| 2016/0100970 A1* | 4/2016 | Brister ............... A61F 5/0046 606/192 |
| 2016/0101263 A1 | 4/2016 | Blumenkranz et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0079548 A1 | 3/2017 | Silverstein et al. |
| 2017/0086785 A1 | 3/2017 | Bjaerum |
| 2017/0100092 A1 | 4/2017 | Kruse et al. |
| 2017/0164923 A1 | 6/2017 | Matsumoto |
| 2017/0172424 A1 | 6/2017 | Eggers et al. |
| 2017/0188839 A1* | 7/2017 | Tashiro ............... A61B 5/0095 |
| 2017/0196535 A1 | 7/2017 | Arai et al. |
| 2017/0215842 A1 | 8/2017 | Ryu et al. |
| 2017/0259013 A1 | 9/2017 | Boyden et al. |
| 2017/0265840 A1 | 9/2017 | Bharat et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0225993 A1 | 8/2018 | Buras et al. |
| 2018/0228465 A1 | 8/2018 | Southard et al. |
| 2018/0235576 A1* | 8/2018 | Brannan ............... A61B 8/488 |
| 2018/0250078 A1* | 9/2018 | Shochat ............... A61B 17/3403 |
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1* | 11/2018 | Lindekugel ............... A61B 90/98 |

(56) References Cited

U.S. PATENT DOCUMENTS

| | | |
|---|---|---|
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1 | 3/2019 | Prevrhal et al. |
| 2019/0105017 A1 | 4/2019 | Hastings |
| 2019/0117190 A1 | 4/2019 | Djajadiningrat et al. |
| 2019/0223757 A1 | 7/2019 | Durfee |
| 2019/0239850 A1 | 8/2019 | Dalvin et al. |
| 2019/0282324 A1 | 9/2019 | Freeman et al. |
| 2019/0298457 A1 | 10/2019 | Bharat |
| 2019/0307516 A1 | 10/2019 | Schotzko et al. |
| 2019/0339525 A1 | 11/2019 | Yanof et al. |
| 2019/0355278 A1 | 11/2019 | Sainsbury et al. |
| 2019/0365348 A1 | 12/2019 | Toume et al. |
| 2020/0041261 A1 | 2/2020 | Bernstein et al. |
| 2020/0069285 A1 | 3/2020 | Annangi et al. |
| 2020/0069929 A1* | 3/2020 | Mason ................. A61M 1/3656 |
| 2020/0113540 A1 | 4/2020 | Gijsbers et al. |
| 2020/0129136 A1 | 4/2020 | Harding et al. |
| 2020/0188028 A1 | 6/2020 | Feiner et al. |
| 2020/0230391 A1 | 7/2020 | Burkholz et al. |
| 2021/0007710 A1 | 1/2021 | Douglas |
| 2021/0045716 A1 | 2/2021 | Shiran et al. |
| 2021/0166583 A1 | 6/2021 | Buras et al. |
| 2021/0307838 A1 | 10/2021 | Xia et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0039777 A1 | 2/2022 | Durfee |
| 2022/0096797 A1 | 3/2022 | Prince |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | McLaughlin et al. |
| 2022/0381630 A1 | 12/2022 | Sowards et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0050061 A1 | 2/2024 | McLaughlin et al. |
| 2024/0058074 A1 | 2/2024 | Misener |
| 2024/0062678 A1 | 2/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 3181083 A1 | 6/2017 |
| EP | 3530221 A1 | 8/2019 |
| JP | 2000271136 A | 10/2000 |
| JP | 2014150928 A | 8/2014 |
| JP | 2018175547 A | 11/2018 |
| KR | 20180070878 A | 6/2018 |
| KR | 20190013133 A | 2/2019 |
| WO | 2013059714 A1 | 4/2013 |
| WO | 2014/115150 A1 | 7/2014 |
| WO | 2014174305 A2 | 10/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2018206473 A1 | 11/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020102665 A1 | 5/2020 |
| WO | 2020/186198 A1 | 9/2020 |
| WO | 2022/031762 A1 | 2/2022 |
| WO | 2022/072727 A2 | 4/2022 |
| WO | 2022/081904 A1 | 4/2022 |
| WO | 2022-203713 A2 | 9/2022 |
| WO | 2022266763 A1 | 12/2022 |
| WO | 2023235435 A1 | 12/2023 |
| WO | 2024010940 A1 | 1/2024 |
| WO | 2024039608 A1 | 2/2024 |
| WO | 2024039719 A1 | 2/2024 |

OTHER PUBLICATIONS

U.S. Appl. No. 17/380,767, filed Jul. 20, 2021 Restriction Requirement dated Dec. 15, 2022.

U.S. Appl. No. 17/397,486, filed Aug. 9, 2021 Non-Final Office Action dated Jan. 23, 2023.

U.S. Appl. No. 17/501,909, filed Oct. 14, 2021 Restriction Requirement dated Feb. 1, 2023.

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/042369 filed Jul. 20, 2021 International Search Report and Written Opinion dated Oct. 25, 2021.

PCT/US2021/045218 filed Aug. 9, 2021 International Search Report and Written Opinion dated Nov. 23, 2021.

PCT/US2021/053018 filed Sep. 30, 2021 International Search Report and Written Opinion dated May 3, 2022.

PCT/US2021/055076 filed Oct. 14, 2021 International Search Report and Written Opinion dated Mar. 25, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].

PCT/US2021/044419 filed Aug. 3, 2021 International Search Report and Written Opinion dated Nov. 19, 2021.

EZono, eZSimulator, https://www.ezono.com/en/ezsimulator/, last accessed Sep. 13, 2022.

Sonosim, https://sonosim.com/ultrasound-simulation/? last accessed Sep. 13, 2022.

U.S. Appl. No. 17/397,486, filed Aug. 9, 2021 Restriction Requirement dated Aug. 12, 2022.

Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).

U.S. Appl. No. 17/380,767, filed Jul. 20, 2021 Non-Final Office Action dated Mar. 6, 2023.

U.S. Appl. No. 17/491,308, filed Sep. 30, 2021 Non-Final Office Action dated Jun. 5, 2023.

U.S. Appl. No. 17/491,308, filed Sep. 30, 2021 Restriction Requirement dated Feb. 27, 2023.

U.S. Appl. No. 17/501,909, filed Oct. 14, 2021 Non-Final Office Action dated Jun. 6, 2023.

PCT/US2023/027147 filed Jul. 7, 2023 International Search Report and Written Opinion dated Oct. 2, 2023.

(56) References Cited

OTHER PUBLICATIONS

PCT/US2023/030160 filed Aug. 14, 2023 International Search Report and Written Opinion dated Oct. 23, 2023.
PCT/US2023/030347 filed Aug. 16, 2023 International Search Report and Written Opinion dated Nov. 6, 2023.
Practical guide for safe central venous catheterization and management 2017 Journal of Anesthesia vol. 34 published online Nov. 30, 2019 pp. 167-186.
U.S. Appl. No. 17/491,308, filed Sep. 30, 2021 Board Decison dated Oct. 25, 2023.
U.S. Appl. No. 17/501,909, filed Oct. 14, 2021 Final Office Action dated Nov. 21, 2023.
PCT/US2023/024067 filed May 31, 2023 International Search Report and Written Opinion dated Sep. 15, 2023.
State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).
U.S. Appl. No. 17/380,767, filed Jul. 20, 2021 Notice of Allowance dated Aug. 31, 2023.
U.S. Appl. No. 17/397,486, filed Aug. 9, 2021 Advisory Action dated Oct. 5, 2023.
U.S. Appl. No. 17/397,486, filed Aug. 9, 2021 Final Office Action dated Aug. 4, 2023.
U.S. Appl. No. 17/491,308, filed Sep. 30, 2021 Final Office Action dated Aug. 29, 2023.
U.S. Appl. No. 17/832,389, filed Jun. 3, 2022 Non-Final Office Action dated Oct. 6, 2023.
U.S. Appl. No. 17/832,389, filed Jun. 3, 2022 Restriction Requirement dated Jul. 13, 2023.
U.S. Appl. No. 17/861,031, filed Jul. 8, 2022 Non-Final Office Action dated Sep. 14, 2023.
U.S. Appl. No. 17/397,486, filed Aug. 9, 2021 Non-Final Office Action dated Mar. 1, 2024.
U.S. Appl. No. 17/478,754, filed Sep. 17, 2021 Restriction Requirement dated Jan. 22, 2024.
U.S. Appl. No. 17/491,308, filed Sep. 30, 2021 Non-Final Office Action dated Mar. 22, 2024.
U.S. Appl. No. 17/501,909, filed Oct. 14, 2021 Advisory Action dated Jan. 24, 2024.
U.S. Appl. No. 17/501,909, filed Oct. 14, 2021 Non-Final Office Action dated Mar. 21, 2024.
U.S. Appl. No. 17/832,389, filed Jun. 3, 2022 Advisory Action dated Apr. 4, 2024.
U.S. Appl. No. 17/832,389, filed Jun. 3, 2022 Final Office Action dated Jan. 25, 2024.
U.S. Appl. No. 17/832,389, filed Jun. 3, 2022 Notice of Allowance dated May 15, 2024.
U.S. Appl. No. 17/861,031, filed Jul. 8, 2022 Final Office Action dated Mar. 15, 2024.
U.S. Appl. No. 17/397,486, filed Aug. 9, 2021 Notice of Allowance dated Jul. 10, 2024.
U.S. Appl. No. 17/478,754, filed Sep. 17, 2021 Non-Final Office Action dated Jul. 1, 2024.
U.S. Appl. No. 17/491,308, filed Sep. 30, 2021 Notice of Allowance dated Jun. 27, 2024.
U.S. Appl. No. 17/501,909, filed Oct. 14, 2021 Final Office Action dated Aug. 5, 2024.
U.S. Appl. No. 17/861,031, filed Jul. 8, 2022 Advisory Action dated Jun. 7, 2024.
U.S. Appl. No. 17/861,031, filed Jul. 8, 2022 Notice of Allowance dated Jul. 3, 2024.
U.S. Appl. No. 18/385,101, filed Oct. 30, 2023 Notice of Allowance dated Aug. 20, 2024.

* cited by examiner

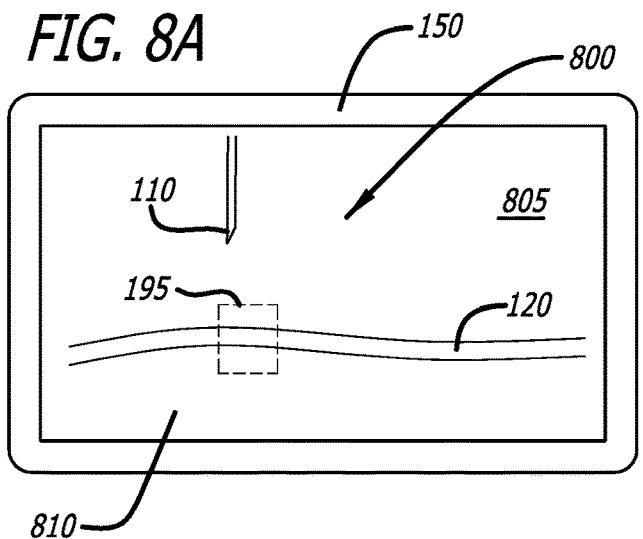
FIG. 8A
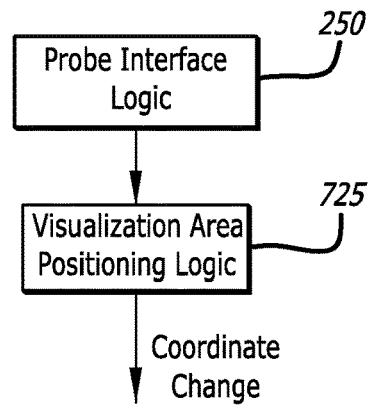
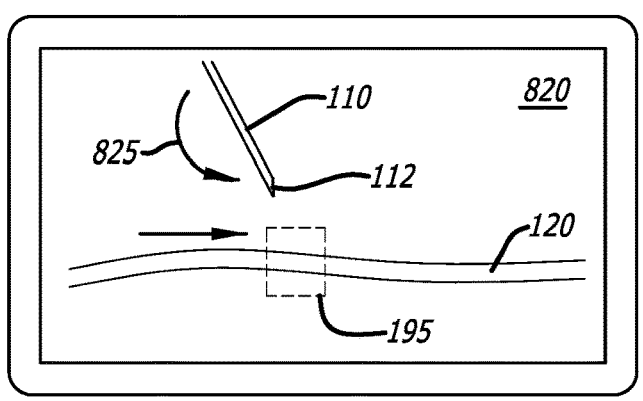
FIG. 8B
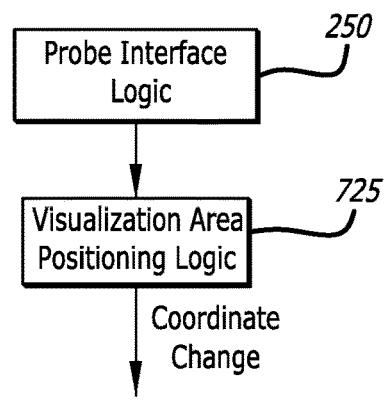
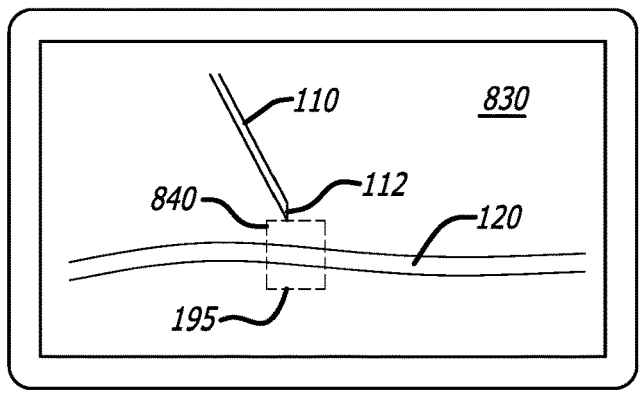
FIG. 8C
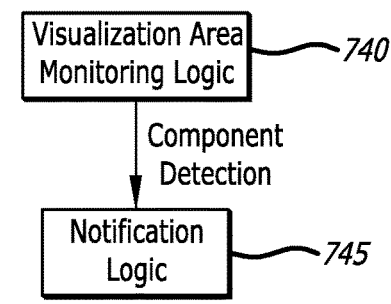

SYSTEMIZED AND METHOD FOR OPTIMIZED MEDICAL COMPONENT INSERTION MONITORING AND IMAGING ENHANCEMENT

PRIORITY

This application claims the benefit of priority to U.S. Provisional Application No. 63/061,120, filed Aug. 4, 2020, which is incorporated by reference in its entirety into this application.

BACKGROUND

In the past, clinicians have relied on various guidance systems, such as ultrasound systems, for assistance with the insertion of a needle into a vasculature (e.g., vessel, artery, etc.) of a patient. However, without a good amount of expertise, a clinician may not be able to easily detect the presence of the needle within an image displayed on an ultrasound system monitor. This lack of real-time detection of the needle location is problematic as the clinician may be required to abruptly move the needle within the subcutaneous tissue in order to penetrate the targeted vasculature. As a result, the patient may experience unnecessary pain during this procedure and the success rate for insertion of a needle into a targeted vasculature (hereinafter, "needle insertion success rate") may be lower than desired.

Conventional needle insertion guidance systems have relied on sensor arrays configured to sense a detectable characteristic related to the needle, such as a magnetic field of a magnetic element included with the needle. In this example, sensors are deployed within an ultrasound probe to continuously detect a magnetic field caused by the magnetic element in order for processing circuitry within the guidance system to calculate the position and orientation of the needle during its advancement. However, for an inexperienced clinician relying solely on the captured ultrasound image, the actual positioning of the needle may differ from the location of the needle rendered on a monitor of the guidance system. This display latency may cause a decrease in needle insertion success rates.

Additionally, artificial intelligence (AI) programs, operating in accordance with machine learning or neural network technologies, have been used to analyze images. However, the operational complexity of AI programs has some correlation to the size of the image under analysis, where the degree of complexity in analyzing certain images rendered for display on a monitor of an ultrasound system may cause a delay in the generation of these images. The delay (latency) in the rendering of the images on the ultrasound system monitor also provides inaccurate information to the clinician as to the current orientation and positioning of the needle.

Hence, low-latency guidance enhancements are needed to improve operability of ultrasound or other guidance systems.

SUMMARY

Briefly summarized, embodiments disclosed herein are directed to a guidance system for medical components such as a needle for example. One embodiment of the guidance system is configured to monitor for the advancement of a medical component (e.g., needle, introducer, catheter, etc.) through sound waves (ultrasound) and/or magnetic fields in accordance with a medical component tracking subsystem. The medical component tracking subsystem may include, but is not limited or restricted to an ultrasound-based or magnetically-based tracking system (e.g., sensor array with console I/O component combination as described below), a tip location subsystem ("TLS") or any other tracking subsystem (e.g., via permanent magnet(s) or electromagnet(s)) of a distal end of the medical component during its advancement through the vasculature as described in U.S. Pat. No. 9,456,766, the contents of which are incorporated by reference herein. The guidance system is further configured with sensory analytic logic to generate visual, audio or haptic feedback in response to detecting the medical component is entering/exiting the targeted vasculature (e.g., vein, artery, etc.).

Another embodiment of the guidance system features artificial intelligence (AI) based visualization controls and AI-based guidance assistance logic. The AI-based visualization controls are configured to generate and position a visualization area, namely the prescribed portion of the total imaging area rendered by the guidance system, based on the orientation and advancement of the medical component. Stated differently, the visualization area is positioned (and re-positioned as necessary) by the AI-based visualization controls to intercept the medical component, as the positioning of the medical component (known through the medical component tracking subsystem), prior to the medical component contacting an outer wall surface of a targeted vasculature.

The AI-based guidance assistance logic is configured to communicate with the medical component tracking subsystem to monitor for entry into or exit from the visualization area in order to notify the clinician of a proximity of the medical component to the targeted vasculature and generate imaging enhancements of the medical component or a portion of the visualization area. The notification of the clinician may be accomplished through audio, visual or haptic (e.g., tactile) feedback through the transmission of signaling to the monitor, an audio device (e.g., speaker) or a probe that generates the visual, audible and tactile notification.

According to one embodiment, a guidance system is described featuring a probe and a console. The console is communicatively coupled to the probe. The console comprises a sensor analytic logic to (i) monitor for a presence of a medical component within a visualization area being a subset of a total imaging area rendered by the guidance system and proximate to a targeted destination and (ii) provide feedback to a device for generating a notification of the presence of the medical component within the visualization area. Herein according to one embodiment, the guidance system monitor for the medical component such as a needle from which a needle reflection is detected when the probe is operating as a part of an ultrasound system. The needle feedback is based on a magnetic field detected by the probe that includes a magnetic element deployed within the medical component.

According to one embodiment of the disclosure, the sensor analytic logic of the guidance system is configured to provide feedback that visibly identifies the presence of the medical component within the visualization area. As one illustrative example, the sensor analytic logic may generate signaling to illuminate a light element within the probe that identifies the medical component is within the visualization area proximate to a vasculature being the targeted destination. As another illustrative example, the sensor analytic logic may provide feedback to an audio device for use in generating an audible notification to identify the presence of the medical component within the visualization area proximate to a vasculature being the targeted destination. As yet another illustrative example, the sensor analytic logic is configured to provide feedback to a haptic feedback device deployed within the probe for use in generating a haptic notification operating as a controlled of the probe.

According to another embodiment of the disclosure, the console further comprises artificial intelligence based (AI-based) visualization controls and AI-based guidance assistance logic. The AI-based visualization controls are configured to generate the visualization area. The AI-based guidance assistance logic is configured to (i) monitor for the presence of the medical component within the visualization area proximate to the targeted destination, (ii) provide the feedback to the device for generating the notification of the presence of the medical component within the visualization area, and (iii) generate and apply an imaging enhancement to at least a portion of imaged data within the visualization area to assist in an advancement of the medical component toward the targeted destination being a vasculature.

As an illustrative embodiment, the imaging enhancement may include a color overlay (e.g., static color adjustment based on entry into visualization area, dynamic color adjustment based on medical component (needle) location, etc.) or image overlay (e.g., increased outline thickness at the distal end or entire portion of the medical component (needle) within the visualization area, enlarged displayed image of the medical component (needle) within visualization area, etc.) of at least a portion of an image of the medical component to provide better clarity as to a position of the medical component. According to another illustrative embodiment, the imaging enhancement includes a virtual representation of the visualization area with the medical component and the vasculature. Besides imaging enhancement, the AI-based guidance assistance logic may be configured to generate a notification, which includes an activation of a light on the probe or a light of the console to identify whether the needle is entering or exiting the targeted destination.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 8A-8E are exemplary embodiments of a first embodiment of the visualization area generated and monitored by the AI-based guidance system of FIG. 7 for enhanced display of a medical component (e.g., needle) based on needle reflection and audio/visual/tactile notification;

DETAILED DESCRIPTION

Figure 1:
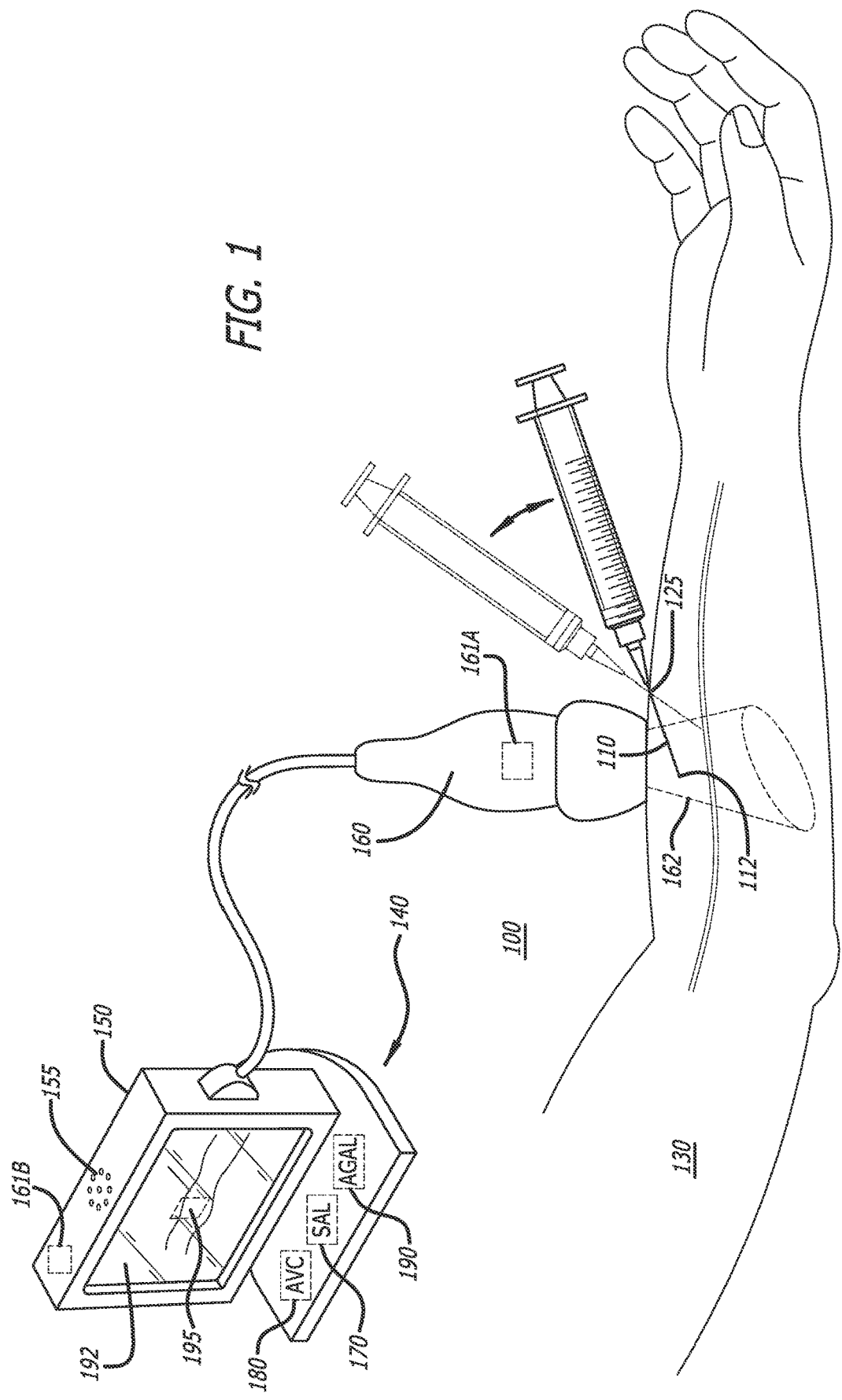
FIG. 1 is an exemplary embodiment of a guidance system for monitoring the insertion of a needle or other medical component into the body of a patient.

Reference will now be made to figures wherein like structures will be provided with like reference designations. It is understood that the drawings are diagrammatic and schematic representations of exemplary embodiments of the invention, and are neither limiting nor necessarily drawn to scale.

Regarding terms used herein, it should be understood the terms are for the purpose of describing some particular embodiments, and the terms do not limit the scope of the concepts provided herein. Ordinal numbers (e.g., first, second, third, etc.) are sometimes used to distinguish or identify different components or operations, and do not supply a serial or numerical limitation. For example, "first," "second," and "third" components or operations need not necessarily appear in that order, and the particular embodiments including such components or operations need not necessarily be limited or restricted to the three components or operations. Similarly, labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The term "logic" is representative of hardware and/or software that is configured to perform one or more functions. As hardware, logic may include circuitry having data processing and/or storage functionality. Examples of such circuitry may include, but are not limited or restricted to a processor, a programmable gate array, a microcontroller, an application specific integrated circuit, combinatorial circuitry, or the like. Alternatively, or in combination with the hardware circuitry described above, the logic may be software in the form of one or more software modules, which may be configured to operate as its counterpart circuitry. The software modules may include, for example, an executable application, a daemon application, an application programming interface (API), a subroutine, a function, a procedure, a routine, source code, or even one or more instructions. The software module(s) may be stored in any type of a suitable non-transitory storage medium, such as a programmable circuit, a semiconductor memory, non-persistent storage such as volatile memory (e.g., any type of random access memory "RAM"), persistent storage such as non-volatile memory (e.g., read-only memory "ROM", power-backed RAM, flash memory, phase-change memory, etc.), a solid-state drive, hard disk drive, an optical disc drive, or a portable memory device.

Unless defined otherwise, all technical and scientific terms used herein have the same meaning as commonly understood by those of ordinary skill in the art.

General Guidance System Architecture

Referring to FIG. 1, an illustrative embodiment of a guidance system 100 is shown, wherein a needle or other medical component 110 may be located and guided, during an ultrasound procedure, magnetic field imaging procedure, or other suitable guidance procedure for example, to access a subcutaneous vasculature 120 of a patient 130. According to this embodiment of the disclosure, the guidance system 100 may be configured to operate as an ultrasound imaging system, although the guidance system 100 may be deployed in accordance with a technology type other than ultrasound.

As illustrated in FIG. 1, the guidance system 100 features a console 140, a monitor 150 and a probe 160. The console 140 may be configured with sensor analytic logic (SAL) 170 that operates in cooperation with a sensor array (see FIGS. 2-3) within the probe 160. The sensor array may capture the position and/or orientation of the medical component 110 through sound waves (ultrasound), where the medical component 110 may include a needle, catheter or an introducer for example. Hereinafter, for simplicity, the medical component 110 may be generally referred to as a "needle" 110.

Additionally, or in the alternative to the console 140, the monitor 150 and the probe 160, a tip location subsystem "TLS" (not shown, see FIG. 2) may be deployed to conduct a real-time determination of a position and/or orientation of the needle 110 through magnetic field analyses. As yet another embodiment, in addition to or in lieu of the sensor analytic logic 170 and/or the TLS, the console 140 may be configured with artificial intelligence (AI) to control operability of the guidance system 100, namely AI-based visualization controls (AVC) 180 and AI-based guidance assistance logic (AGAL) 190 to render imaging enhancements that assist in guiding the clinician in the advancement of the needle 110, as described below.

As shown in FIG. 1, the guidance system 100, operating as an ultrasound imaging system for example, is configured to generate an image of a targeted internal portion of a body of a patient immediately prior and subsequent to percutaneous insertion of the needle 110. For one embodiment, such as guided needle advancement for example, the guidance system 100 may be employed to image a region surrounding the vasculature 120 during and/or subsequent to percutaneous insertion of the needle 110 to access the targeted vasculature 120. As described below, insertion of the needle 110 may be performed prior to insertion of a catheter into a portion of the vasculature 120 of the patient 130. It is appreciated, however, that insertion of the needle 110 into the patient 130 can be performed for a variety of medical purposes.

According to one embodiment of the disclosure, the sensor analytic logic 170 receives orientation metrics from the sensor array, and in response to entry of the needle 110 into a region of interest (ROI) defined by the vasculature 120 itself, the sensor analytic logic 170 is configured to generate a notification regarding entry into the vasculature. More specifically, the sensor analytic logic 170 is configured to monitor for a change of state of the needle 110 (intra-vasculature vs. extra-vasculature). In response to the change in state, the sensor analytic logic 170 may be configured to generate signaling that would cause the monitor 150 to render a visual notification of the state change for display or activation of a light on the probe 160 or console 140 to identifying whether the needle is entering or exiting the vasculature 120. Additionally, or in the alternative, the sensor analytic logic 170 may be configured to generate signaling that would cause an audio device (e.g., speaker 155) to emit an audible notification in response to any state change, such as a first type of audible notification (e.g., beep, tone, etc.) in response to a transition from an extra-vasculature state to an intra-vasculature state and a second type of audible notification in response to a transition an intra-vasculature state to an extra-vasculature state.

Besides visual or audio notifications, again in addition to or in the alternative of the visual and/or audible notification, the sensor analytic logic 170 may be configured to generate signaling that would cause a haptic feedback device within the probe 160 to provide a physical warning (e.g., vibration and/or another force-based feedback) as a haptic notification. The haptic feedback device as described below and illustrated in FIG. 3.

According to another embodiment of the disclosure, operating separately or in combination with the sensory analytic logic 170, the AI-based visualization controls 180 are configured to receive the orientation metrics of the needle 110 from the probe 160 and generate and locate a visualization area 195 based on these orientation metrics. As shown, the visualization area 195 corresponds to a portion of a total imaging area 192 rendered by the guidance system 100. For this embodiment, the visualization area 195 is substantially lesser in size (e.g., less than a $\frac{1}{10}^{th}$ of size) than the total imaging area 192, which may include the image captured from a sound beam 162 emitted from the probe 160 and rendered for display on the monitor 150 of the guidance system 100. The sizing of the visualization area 195 may be static or dynamic (e.g., based on needle gauge, medical component type, etc.). Also, the location of the visualization area 195 may be altered based on the position, orientation and advancement of the needle 110 so as to intercept advancement of the needle 110 prior to contact with an outer wall surface of the targeted vasculature 120.

In particular, the guidance system 100 enables the position, orientation, and advancement of the medical component 110 (e.g., needle) to be superimposed, in real-time, on the ultrasound image of the vasculature 120, thus enabling a clinician to accurately guide the needle 110 to the vasculature 120, as shown in more detail in FIGS. 8A-8E. Furthermore, for some embodiments, imaging enhancements may be applied to a portion of the imaged data, such as a color overlay that may be static in color change or dynamic based on its presence and/or location of the medical component within the visualization area. The imaging enhancement may include, additionally or in the alternative, an image overlay of at least a portion of an image of the needle 110 (e.g., thicker outline, enlarged sizing of certain portions of the needle such as the portions of the needle within the visualization area) to provide better clarity as to its position. Another imaging enhancement may include generation of a virtual representation of the visualization area (with needle 110 and vasculature 120). Other imaging enhancements may be deployed where the enhancements are designed to assist the clinician in the advancement of the needle 110.

Furthermore, for this embodiment, the guidance system 100 tracks the position of the needle 110 in accordance with numerous degrees of motion during advancement as illustrated by dashed lines in FIG. 1. The position of the needle 110, from at least the insertion to subsequent upward or downward angular adjustment of the needle 110, may be represented by the following information: xyz spatial coordinate space, pitch of the needle 110, and/or yaw (e.g., orientation) of the needle 110. Herein, for some embodiments, this information may constitute the orientation metrics provided to the AI-based visualization controls 180. In other embodiments, the orientation metrics may be based, at least in part, on this information or a portion thereof.

Such tracking enables a distal end (tip) 112 of the needle 110 to be guided and placed with relatively high accuracy despite movement of the needle 110. Also, based on the information gathered during the tracking operations (e.g., needle reflection, etc.), the location of the needle 110 may be determined, where the AI-based visualization controls 180 are configured to generate and reposition the visualization area 195 to intercept the distal end 112 of the needle 110 moving towards the vasculature 120.

According to one embodiment of the disclosure, the AI-based guidance assistance logic 190 may be configured to monitor the position of the needle 110 for entry into or exit from the visualization area 195. As shown, the visualization area 190 may be represented as a "bounding box," namely any shaped region located proximate to and potentially inclusive of the vasculature 120 along a computed path for advancement of the needle 110. Upon entry into the visualization area 195, the AI-based guidance assistance logic 190 notifies the clinician of the proximity of the needle 110 to a targeted vasculature. The notification may be accomplished through visual, audible and/or haptic (e.g., tactile) feedback signaling provided to the monitor 150, the audio device 155 and/or the sensors within the probe 160.

Additionally, upon entry into the visualization area 195, the AI-based guidance assistance logic 190 generates additional imaging enhancements to assist in the visualization of the needle 110 in close proximity to the vasculature 120. For example, one of the imaging enhancements may include a color and/or image overlay of an image of the needle 110 (as described above) to provide better clarity as to its position. Another imaging enhancement may include activation of a light source (e.g., light emitting diode, etc.) accompanying the needle 110, installed on the probe 160 (light 161A) or installed on the console 140 (light 161B). Yet another imaging enhancement may include the generation of a secondary (virtualized) image with appropriate magnification to provide a split-screen view of the needle 110 proximate to and engaging with the vasculature 120.

As mentioned, placement of a medical component (e.g., needle) 110 into the patient vasculature 120 at the insertion site 125 may be performed out-of-plane, where the needle 110 enters the skin away from the probe 160, and is aimed at a plane of an ultrasound beam 162 emitted from the probe 160. With this approach, just the distal tip 112 of the needle 110 would be visualized and a remainder of the needle 110 may be off screen at the time of detection.

Enhanced Guidance System with Sensor-Based Feedback

Embodiments of the present invention described herein are generally directed to the guidance system 100 for locating and guiding the medical component (e.g., needle, etc.) during ultrasound-based or other suitable procedures in accessing the subcutaneous vasculature of a patient. In one embodiment, the guidance system 100 tracks the position of the needle in five degrees of motion: x, y, and z spatial coordinate space, pitch, and yaw (e.g., orientation). Such tracking enables the needle to be guided and placed with relatively high accuracy.

Figure 2:
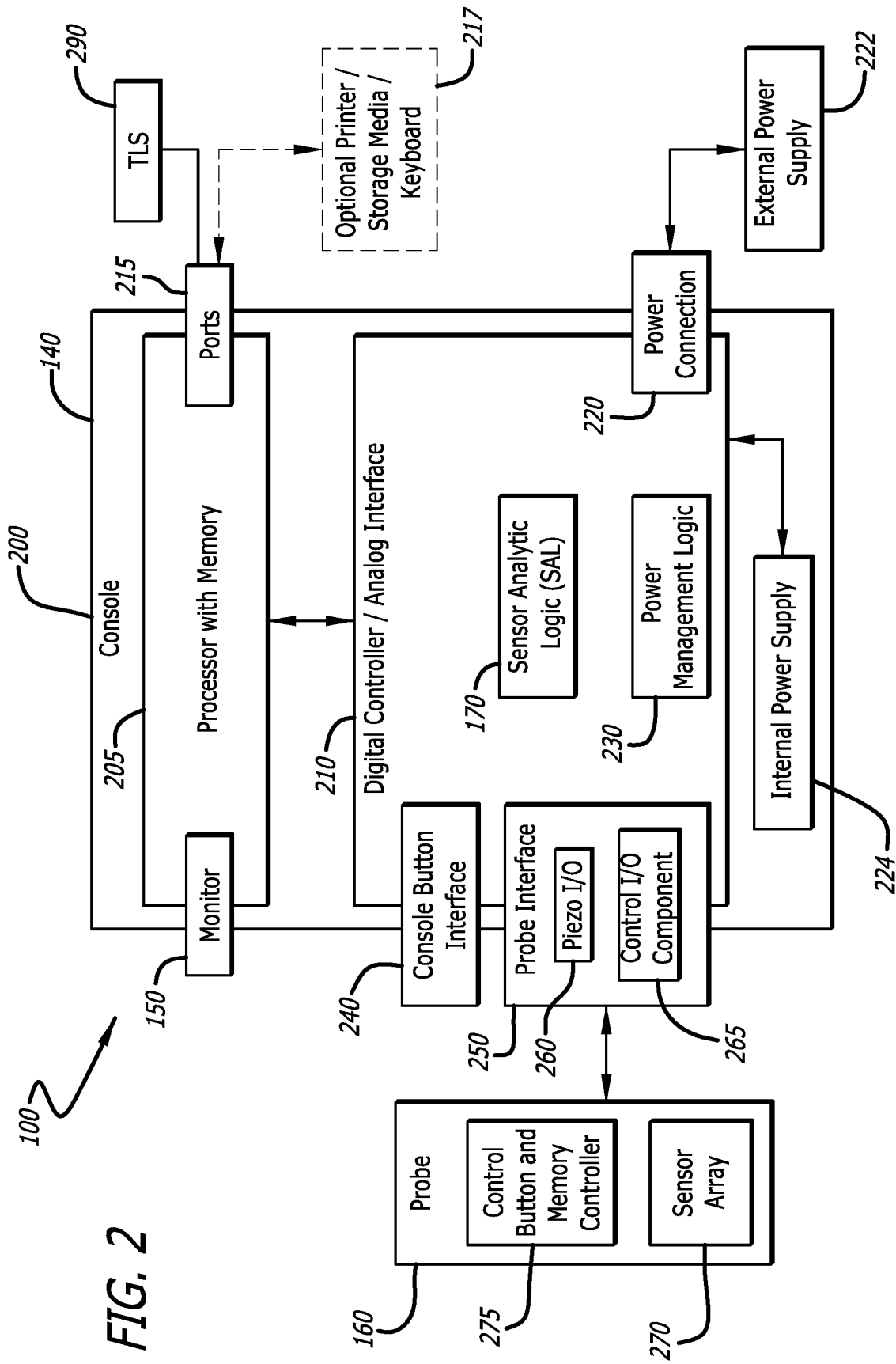
FIG. 2 is an exemplary block diagram depicting various elements of an ultrasound-based guidance system for needles and other medical components, according to a first embodiment of the guidance system.

As shown in FIG. 2, various components of the ultrasound-based guidance system 100 is shown configured in accordance with one embodiment of the present invention. As shown, the guidance system 100 generally includes the console 140, the monitor 150, a TLS sensor 290 and the probe 160, each of which is described in further detail below. Herein, the console 140 may include a housing 200 to protect a variety of components of the system 100 from environmental conditions and may be adapted in accordance with one of a variety of forms. For example, a processor, including a memory such as a non-volatile memory (e.g., electrically erasable programmable read only memory (flash), battery-backed random access memory, etc.) 205, is included in the console 140 for controlling functionality of the guidance system 110, thus acting as a control processor. A digital controller/analog interface 210 is also included within the console 140 and is in communication with both the processor 205 and certain system components that govern interfacing between the probe 160 and other system components.

The guidance system 100 further includes ports 215 for connection with additional components such as optional components 217 including a printer, storage media, keyboard, etc. The ports 215, according to one embodiment of the disclosure, may include Universal Serial Bus (USB) ports, though other port types or a combination of port types can be used for this and the other interfaces connections described herein. A power connection 220 is included with the console 140 to enable operable connection to an external power supply 222. An internal power supply (e.g., battery) 224 can also be employed, either with or exclusive of the external power supply 222. Power management logic 230 is included within the digital controller/analog interface 205 of the console 140 to regulate power use and distribution.

According to one embodiment of the disclosure, the monitor 150 may be integrated into the console 140 and may be used to display information to the clinician during the placement procedure, such as an ultrasound image of a region of interest of the patient that is captured by the probe 160. In another embodiment, however, the monitor 150 may be separate from the console 140. For this embodiment of the disclosure, the monitor 150 is a liquid crystal display (LCD) device.

In one embodiment, a console interface logic 240 and/or probe interface logic 250 is(are) included on the probe 160, which can be used to enable the clinician to select a desired mode to the monitor 150 for assisting in the needle placement procedure. Signaling from the probe 160 are routed to the console 140 via the probe interface logic 250. The probe interface 250 includes a piezoelectric ("piezo") input/output (I/O) component 260 and a control I/O component 265. The piezo I/O component 260 interfaces with a sensor (piezo) array 270 that captures an image through sound waves, including needle reflection that identifies the position, orientation, and movement of the needle 110 during ultrasound imaging procedures. The control I/O component 265 interfaces with a control button and memory controller 275 to receive operational commands therefrom.

The TLS sensor 290 is employed by the guidance system 100 to detect a magnetic field produced by the magnetic elements of the medical component such as the needle 110 or a stylet within the needle 110. The TLS sensor 290 may be placed in proximity to the region of interest for the patient during needle insertion. During advancement of the needle, the TLS sensor 290 detects the magnetic field associated with the magnetic elements, which provides information to the clinician as to the position and orientation of the medical component (needle) 110 during its advancement.

The TLS sensor 290 is operably connected to the console 140 of the guidance system 100 via one or more of the ports 215. Detection by the TLS sensor 290 of the magnetic elements within the needle 110 is graphically displayed on the monitor 150 of the console 140 during a modality (TLS mode) set by the probe 160. In this way, clinician for controlling the guidance system 100 may activate the TLS sensor 290 or establish communications between the TLS sensor 290 and the monitor 150.

Figure 3:
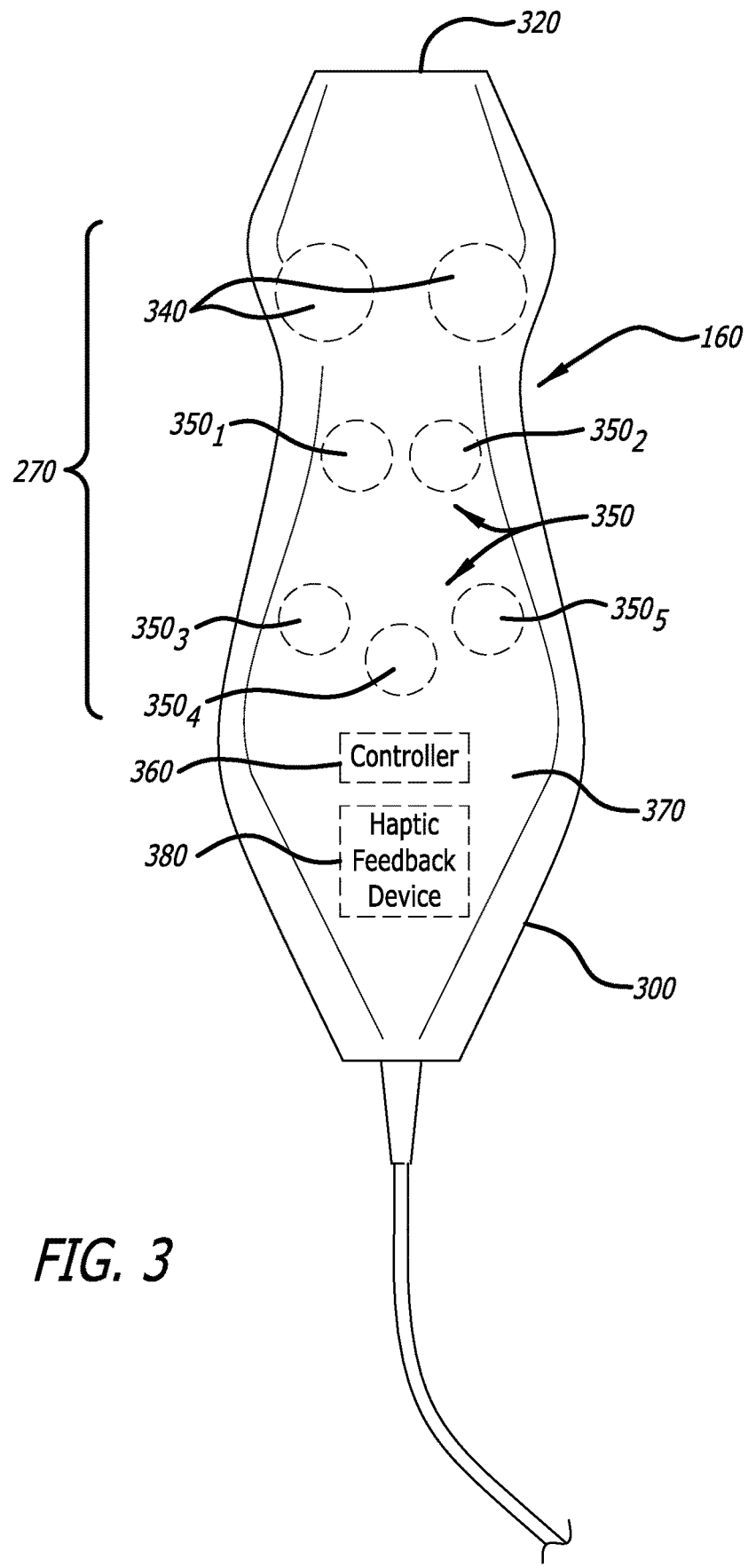
FIG. 3 is a top plan view of the ultrasound probe of the guidance system of FIG. 2.

Referring now to FIG. 3, an exemplary embodiment of the probe 160 of FIGS. 1-2 is shown. The probe 160 is employed in connection with ultrasound-based visualization of a vasculature, such as a vein, in preparation for insertion of the medical component 110 (e.g., needle, catheter, etc.) into the vasculature. Such visualization gives real time ultrasound guidance and assists in reducing complications typically associated with such introduction of the needle 110, including inadvertent arterial puncture, or the like.

In particular, according to one embodiment of the disclosure, the probe 160 includes a housing 300 that features an interface 310 with externally accessible control buttons 315 to enable a clinician to control operability of the guidance system 100 without the reach outside of the sterile field. As shown, the housing 300 encapsulates the sensor array 270 (inclusive of a piezoelectric array 340 and/or magnetic field sensors 350) a controller 360, and a haptic feedback device 380. However, it is contemplated that the sensor array 270 may be positioned outside of the housing 300 and attached to the probe 160.

As shown, located proximate to a head section 320 of the housing 300, the piezoelectric array 340 may be configured to produce ultrasonic pulses and to receive echoes thereof after reflection by the patient's body when the head section 320 is placed against the patient's skin proximate the prospective insertion site 125 as shown in FIG. 1.

As further shown in FIG. 3, including non-volatile memory such as flash memory for example, the controller 360 is for governing button and probe operations. The controller 360 is in operable communication with the probe interface 250 of the console 200, which includes the piezo I/O component 260 and the control I/O component 265. The piezo I/O component 260 is configured for interfacing with the piezoelectric array 340 of the sensor array 270 while the control I/O component 265 is configured for interfacing with the controller 360.

As further seen in FIG. 3, the sensor array 270 is configured to detect the position, orientation, and movement of the needle 110 during ultrasound imaging procedures, such as those described above. As will be described in further detail below, the sensor array 270 includes magnetic field sensors 350, namely a plurality of magnetic sensors $350_1$-$350_N$ (N≥2) embedded within the housing 300 of the probe 160. According to one embodiment of the disclosure, the sensors $350_1$-$350_N$ are configured to detect a magnetic field associated with the needle 110 and enable the system 100 to track the needle 110. Though configured here as magnetic sensors, it is appreciated that the sensors $350_1$-$350_N$ can be sensors of other types and configurations, as will be described. Also, the sensors $350_1$-$350_N$ may be deployed in a component separate from the probe 160, such as a separate handheld device. In the present embodiment, the sensors $350_1$-$350_N$ are disposed in a planar configuration below a top face 370 of the probe 160, though it is appreciated that the sensors $350_1$-$350_N$ can be arranged in other configurations, such as in an arched or semi-circular arrangement.

In the present embodiment, each of the sensors $350_1$-$350_N$ may correspond to a three-dimensional sensor such as three orthogonal sensor coils for enabling detection of a magnetic field in three spatial dimensions. Additionally, or in the alternative, the sensors $350_1$-$350_N$ may be configured as Hall-effect sensors, though other types of magnetic sensors could be employed. Additionally, or in the alternative, a plurality of one-dimensional magnetic sensors can be included and arranged as desired to achieve 1-, 2-, or 3-D detection capability For this embodiment of the disclosure, five sensors $350_1$-$350_5$ are included as part of the sensor array 270 so as to enable detection of the needle 110 in not only the three spatial dimensions (i.e., X, Y, Z coordinate space), but also the pitch and yaw orientation of the needle 110 itself. Note that in one embodiment, orthogonal sensing components of two or more of the sensors $350_1$-$350_N$ enable the pitch and yaw attitude of the medical component 110, and thus the needle 110, to be determined. However, in other embodiments, fewer or more sensors can be employed in the sensor array 270. More generally, it is appreciated that the number, size, type, and placement of the sensors $350_1$-$350_N$ can vary from what is explicitly shown here.

The haptic feedback device 380 includes refers to one or more devices that, when activated, creates an experience of touch by applying forces, vibrations or motions to the clinician handling the probe 160. According to one embodiment of the disclosure, the haptic feedback device 380 may be configured to support a haptic feedback corresponding to a vibration and/or a force feedback. The use of vibration may rely on an actuator including an unbalanced weight attacked to an axially rotatable shaft such as an eccentric rotating mass (ERM) actuator. When the actuator is activated, as the shaft rotates, the rotation of this irregular mass causes the actuator and the attached device to shake. Similarly, force feedback relies on motors to manipulate the movement of an item held by the user in order to simulate forces applied on that item.

Figure 4A:
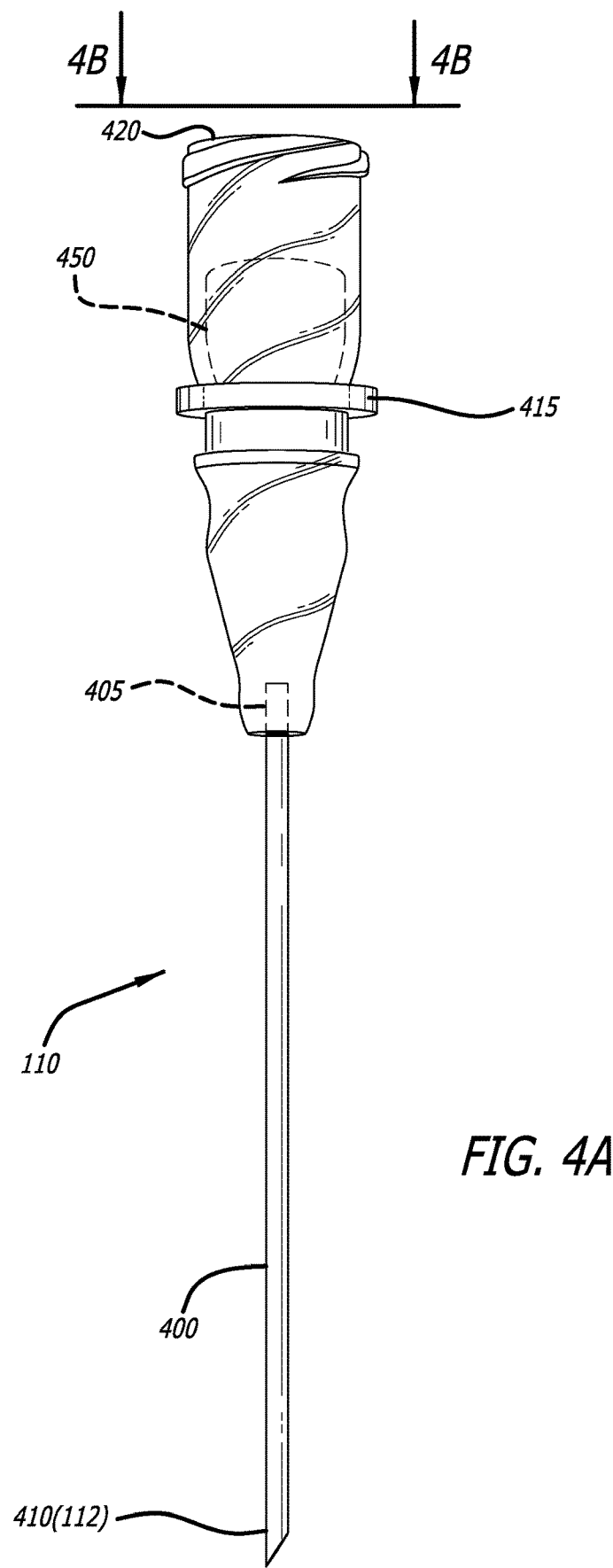
FIG. 4A is a side view of a needle for use with the guidance system of FIG. 2, according to one embodiment.
Figure 4B:
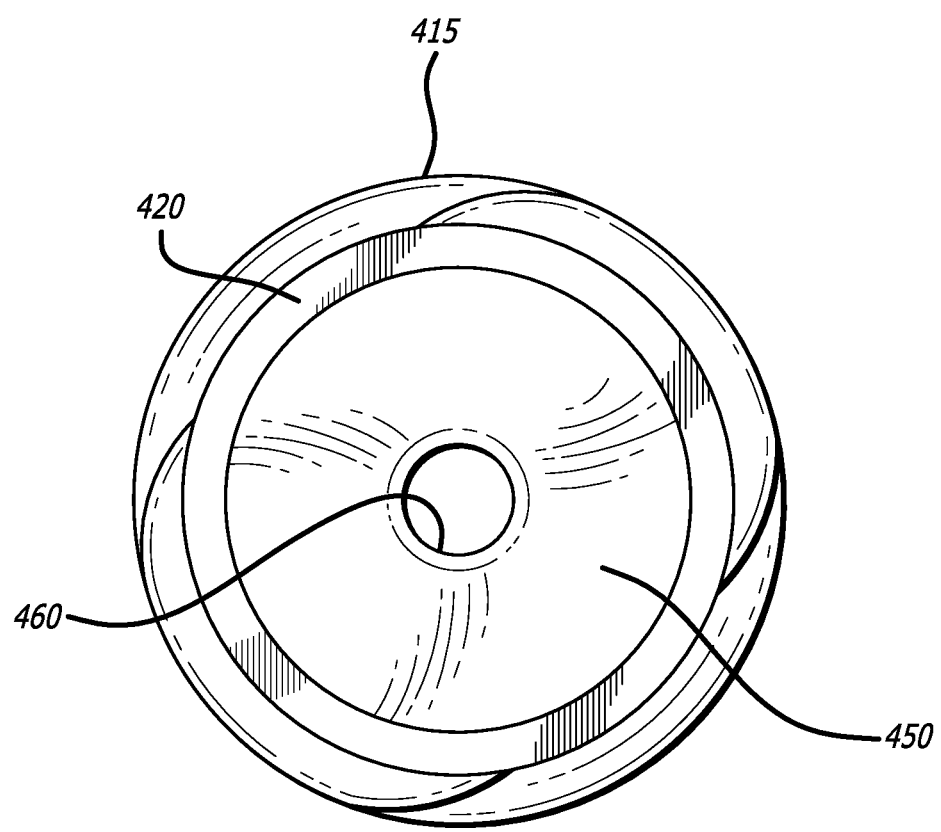
FIG. 4B is an end view of the needle of FIG. 4A.

FIGS. 4A and 4B show details of one example of the needle 110 that can be used in connection with the guidance system 100 in accessing a targeted internal body portion of the patient, as shown in FIG. 1, according to one embodiment. In particular, the needle 110 includes a hollow cannula 400, which defines a proximal end 405 and a distal end 410. A hub 415 is attached to the proximal end 405 of the cannula 400 and includes an open end 420 that is configured as a connector for connecting with various devices, in the present embodiment. Indeed, the open end 420 of the hub 415 is in communication with the hollow cannula 400 such that a guide wire, stylet, or other component may be passed through the hub 415 into the cannula 400.

As shown in FIGS. 4A and 4B, a magnetic element 450 is included with the hub 415. As shown in detail in FIG. 4B, the magnetic element 450 in the present embodiment is a permanent magnet, including a ferromagnetic substance for instance, and is ring-shaped so as to define hole 460 that is aligned with the hollow cannula 400. So configured, the magnetic element 450 produces a magnetic field that is detectable by the sensor array 270 of the ultrasound probe 160 (or perhaps the TLS 290) so as to enable the location, orientation, and movement of the needle 110 to be tracked by the system 100, as described further below.

In other embodiments, it is appreciated that many other types, numbers, and sizes of magnetic elements can be employed with the needle 110 or other medical component to enable tracking thereof by the present guidance system.

Figure 5A:
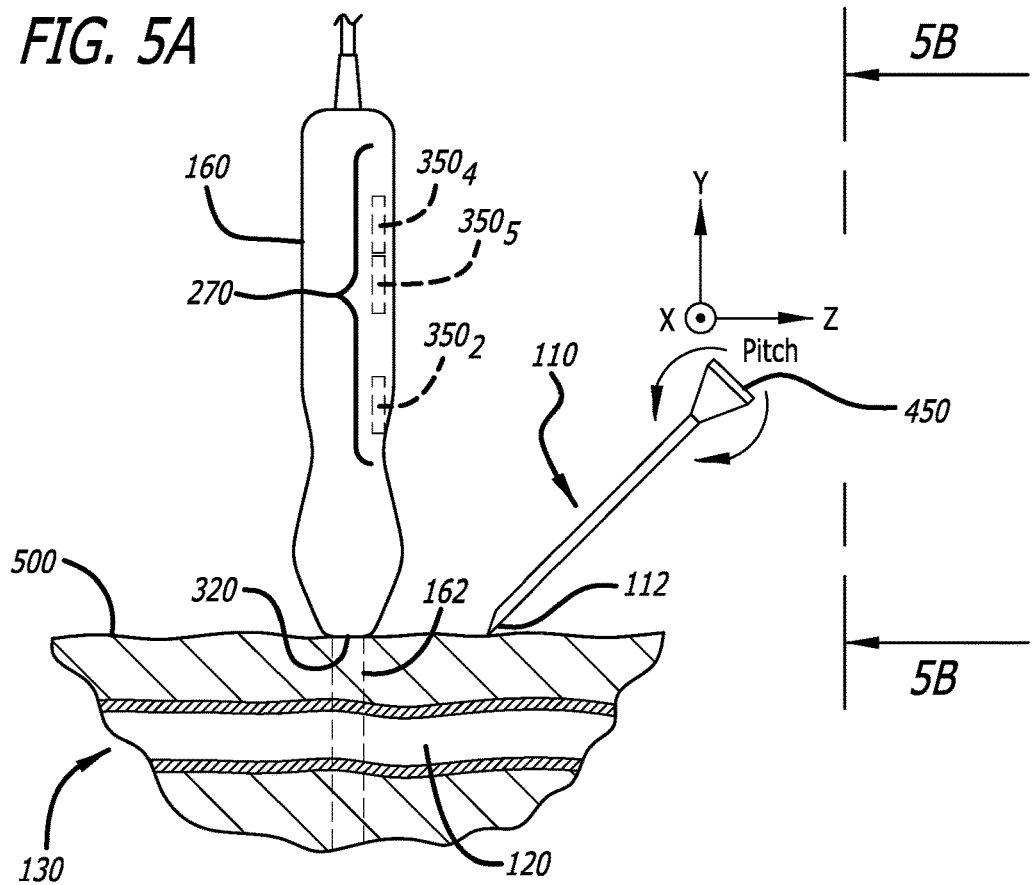
FIGS. 5A and 5B are simplified views of the ultrasound probe of the guidance system of FIG. 2 being used to guide the needle toward a vessel within the body of a patient.
Figure 5B:
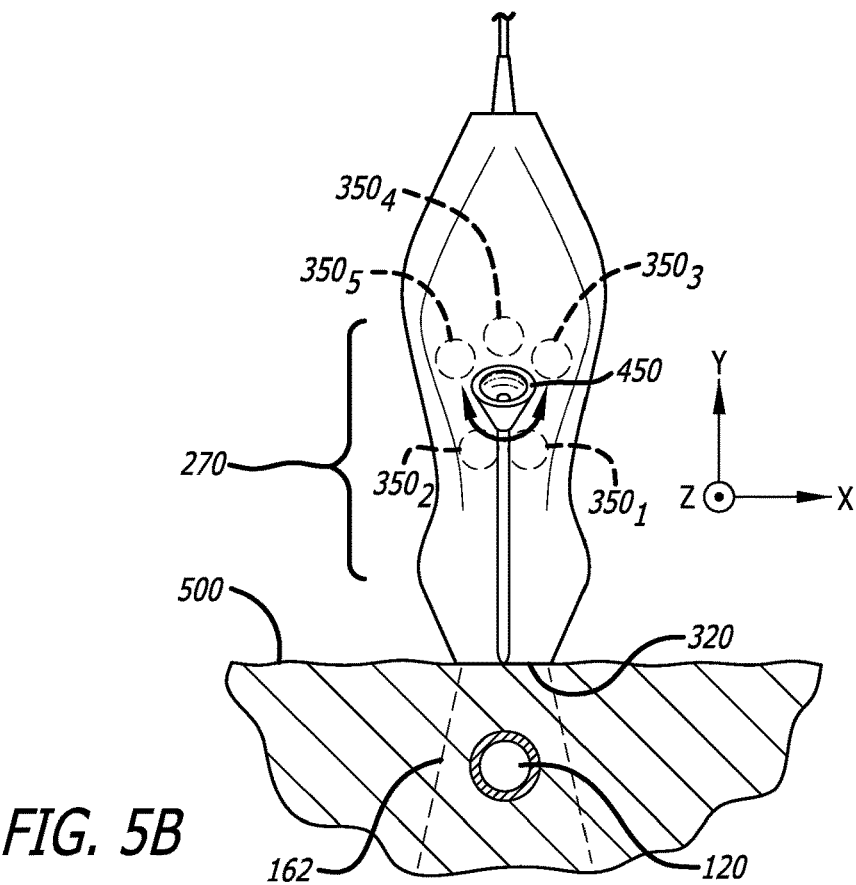

Reference is now made to FIGS. 5A and 5B, which show the ultrasound probe 160 of the system 100 and the needle 110 in position and ready for insertion thereof through a skin surface 500 of a patient to access a targeted internal body portion. In particular, the probe 160 is shown with its head section 320 placed against the patient skin and producing the ultrasound beam 162 so as to ultrasonically image a portion of the vasculature 120 beneath the patient skin surface 500. The ultrasonic image of the vasculature 120 can be depicted on the monitor 150 of the system 100 (FIG. 1).

As mentioned above, the system 100 in the present embodiment is configured to detect the position, orientation, and movement of the needle 110 described above. In particular, the sensor array 270 of the probe 160 is configured to detect a magnetic field of the magnetic element 450 included with the needle 110. Each of the sensors $350_1$-$350_N$ of the sensor array 270 is configured to spatially detect the magnetic element 450 in three-dimensional space. Thus, during operation of the system 100, magnetic field strength data of the needle's magnetic element 450 sensed by each of the sensors $350_1$-$350_N$ is forwarded to a processor, such as the processor 205 of the console 140 (FIG. 1), which computes in real-time the position and/or orientation of the magnetic element 450.

Specifically, and as shown in FIGS. 5A and 5B, the position of the magnetic element 450 in X, Y, and Z coordinate space with respect to the sensor array 270 can be determined by the system 100 using the magnetic field strength data sensed by the sensors $350_1$-$350_N$. Moreover, FIG. 5A shows that the pitch of the magnetic element 450 can also be determined, while FIG. 5B shows that the yaw of the magnetic element 450 can be determined. Suitable circuitry of the probe 160, the console 140, or other component of the system can provide the calculations necessary for such position/orientation. In one embodiment, the magnetic element 450 can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties.

Figure 6A:
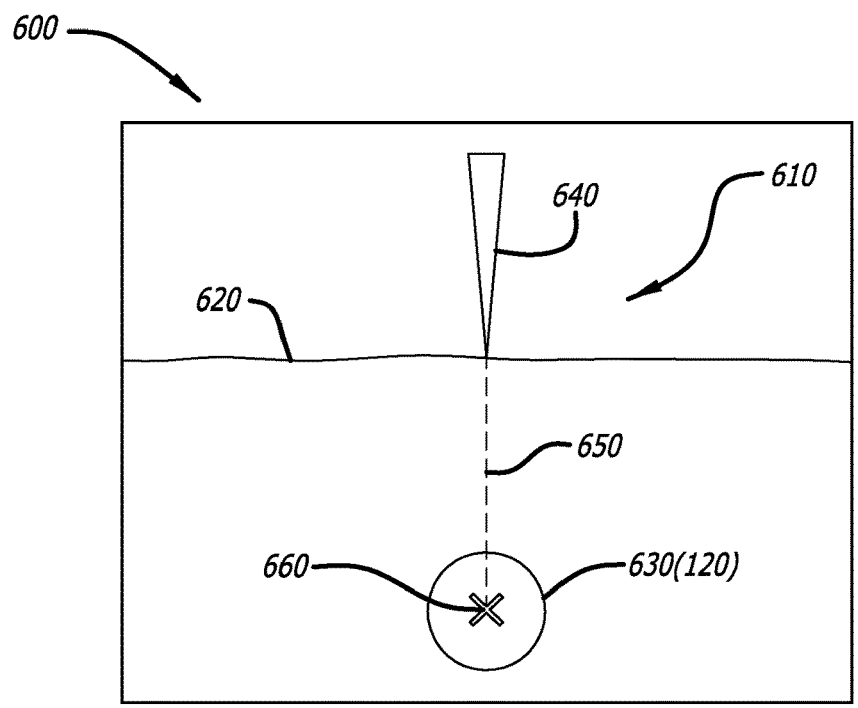
FIGS. 6A and 6B show possible screenshots for depiction on the display of the guidance system, showing the position and orientation of a needle according to one embodiment.
Figure 6B:
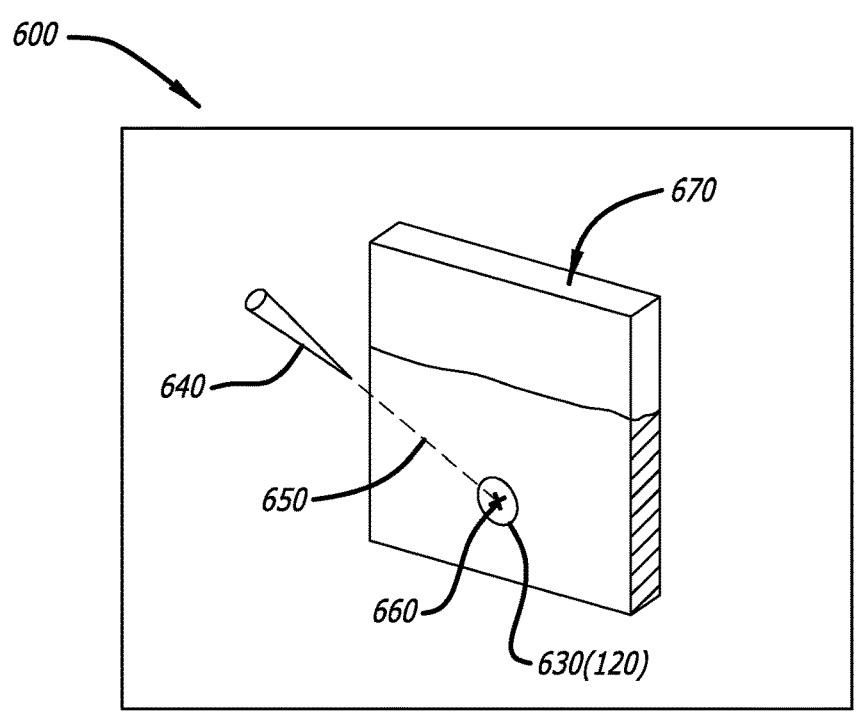

The above position and orientation information determined by the system 100, together with the length of the cannula 400 and position of the magnetic element 450 with respect to the distal needle tip 112 as known by or input into the system, enable the system to accurately determine the location and orientation of the entire length of the needle 110 with respect to the sensor array 270. Optionally, the distance between the magnetic element 450 and the distal needle tip 112 is known by or input into the system 100. This in turn enables the system 100 to superimpose an image of the needle 110 on to an image produced by the ultrasound beam 162 of the probe 160. FIGS. 6A and 6B show examples of such a superimposition of the needle 110 onto an ultrasound image 600.

Herein, FIGS. 6A and 6B each show a screenshot 600 that can be depicted on the monitor 150 (FIG. 1), for instance. In FIG. 6A, an ultrasound image 610 is shown, including depiction of the patient skin surface 620, and the subcutaneous vessel 630. The ultrasound image 610 corresponds to an image acquired by the ultrasound beam 162 shown in FIGS. 5A and 5B, for instance.

The screenshot 600 further shows a needle image 640 representing the position and orientation of the actual needle 110 as determined by the guidance system 100 as described above. Because the system 100 is able to determine the location and orientation of the needle 110 with respect to the sensor array 270, the guidance system 100 is able to accurately determine the position and orientation of the needle with respect to the ultrasound image 610 and superimpose it thereon for depiction as the needle image 640 on the monitor 150. Coordination of the positioning of the needle image 640 on the ultrasound image 610 is performed by suitable algorithms executed by the processor 205 or other suitable component of the guidance system 100.

The sensors $350_1$-$350_N$ are configured to continuously detect the magnetic field of the magnetic element 450 of the needle 110 during operation of the guidance system 100. This enables the guidance system 100 to continuously update the position and orientation of the needle image 640 for depiction on the monitor 150. Thus, advancement or other movement of the needle 110 is depicted in real-time by the needle image 640 on the monitor 150. Note that the guidance system 100 is capable of continuously updating both the ultrasound image 610 and the needle image 640 on the monitor 150 as movements of the probe 160 and the needle 110 occur during a placement procedure or other activity.

FIG. 6A further shows that in one embodiment the system 100 can depict a projected path 650 based on the current position and orientation of the needle 110 as depicted by the needle image 640. The projected path 650 assists a clinician in determining whether the current orientation of the needle 110, as depicted by the needle image 640 on the monitor 150, will result in arriving at the desired internal body portion target, such as the vasculature 120 shown here. Again, as the orientation and/or position of the needle image 640 changes, the projected path 650 is correspondingly modified by the system 100. A target 660, indicating an intended destination for the needle. As shown in FIG. 6A, in the present example, the target 660 is located within the vasculature 120 depicted in the ultrasound image 610. Note that the position of the target 660 on the monitor 150 can also be modified as the needle 110 and/or the ultrasound image 610 are adjusted.

FIG. 6B shows that, in one embodiment, the screenshot 600 can be configured such that the ultrasound image 610 and the needle image 640 are oriented so as to be displayed in a three-dimensional aspect 670. This enables the angle and orientation of the needle 110, as depicted by the needle image 640, to be ascertained and compared with the intended target imaged by the ultrasound image 610. It should be noted that the screenshots 600 are merely examples of possible depictions produced by the system 100 for display; indeed, other visual depictions can be used. Note further that the particular area of the body being imaged is merely an example; the system can be used to ultrasonically image a variety of body portions, and should not be limited to what is explicitly depicted in the accompanying figures. Further, the system as depicted and described herein can be included as a component of a larger system, if desired, or can be configured as a stand-alone device. Also, it is appreciated that, in addition to providing visual information rendered on the monitor 150, aural information, such as beeps, tones, etc., can also be employed by the system 100 to assist the clinician during positioning and insertion of the needle into the patient.

As mentioned above, in one embodiment it is necessary for the system 100 to know the total length of the needle 110 and the location of the magnetic element 450 thereon in order to enable an accurate depiction of the needle image 640 and other features of the screenshots 600 of FIGS. 6A and 6B to be made. The system 100 can be informed these and/or other pertinent parameters in various ways, including scanning by the system of a barcode included on or with the needle, the inclusion of a radiofrequency identification ("RFID") chip with the needle for scanning by the system, color coding of the needle, manual entry of the parameters by the clinician into the system, etc.

In one embodiment, a length of the needle 110 (or other aspect of a medical component) can be determined by measurement by the probe/system 160/100 of a characteristic of the magnetic element 450 of FIG. 4A, such as its field strength. For instance, in one embodiment, the magnetic element 450 of the needle 110 can be positioned at a predetermined distance from the probe 160 or at a predetermined location with respect to the probe 160. With the magnetic element 450 so positioned, the sensor array 270 of the probe 160 detects and measures the field strength of the magnetic element 450. The system 100 can compare the measured field strength with a stored list of possible field strengths corresponding to different lengths of needles. The system 100 can match the two strengths and determine the needle length. The needle location and subsequent needle insertion can then proceed as described herein. In another embodiment, instead of holding the magnetic element 450 stationary at a predetermined location, the magnetic element 450 can be moved about the probe 160 such that multiple field strength readings are taken by the probe 160. Aspects that can be modified so as to impart different field strengths to a set of magnetic element include size, shape, and composition of the magnetic element, etc.

Further details are given here regarding use of the system 100 in guiding a needle or other medical device in connection with ultrasonic imaging of a targeted internal body portion ("target") of a patient, according to one embodiment. With the magnetic element-equipped needle 110 positioned a suitable distance (e.g., two or more feet) away from the ultrasound probe 160 including the sensor array 270, the probe 160 is employed to ultrasonically image, for depiction on the monitor 150 of the system 100, the target within the patient that the needle 110 is intended to intersect via percutaneous insertion. A calibration of the system 100 is then initiated, in which algorithms are executed by the processor 205 of the console 140 to determine a baseline for any ambient magnetic fields in the vicinity of where the procedure will be performed. The system 100 is also informed of the total length of the needle 110, and/or position of the magnetic element with respect to the distal needle tip 112 such as by user input, automatic detection, or in another suitable manner, as has been discussed above.

The needle 110 is then brought into the range of the sensors $350_1$-$350_N$ of the sensor array 270 of the probe 160. Each of the sensors $350_1$-$350_N$ detects the magnetic field strength associated with the magnetic element 450 of the needle 110, which data is forwarded to the processor 205. In one embodiment, such data can be stored in memory until needed by the processor 205. As the sensors $350_1$-$350_N$ detect the magnetic field, suitable algorithms are performed by the processor 205 to calculate a magnetic field strength of the magnetic element 450 of the needle 110 at predicted points in space in relationship to the probe. The processor 205 then compares the actual magnetic field strength data detected by the sensors $350_1$-$350_N$ to the calculated field strength values. Note that this process is further described in the U.S. patents identified above. This process can be iteratively performed until the calculated value for a predicted point matches the measured data. Once this match occurs, the magnetic element 450 has been positioned in three-dimensional space. Using the magnetic field strength data as detected by the sensors $350_1$-$350_N$, the pitch and yaw (i.e., orientation) of the magnetic element 450 can also be determined. Together with the known length of the needle 110 and the position of the distal tip 112 of the needle 110 with respect to the magnetic element 450, this enables an accurate representation of the position and orientation of the needle can be made by the system 100 and depicted as a virtual model, i.e., the needle image 640. The representation may be provided as orientation metrics provided to the sensor analytic logic 170 of FIG. 2 or the AI-based visualization logic 180 of FIG. 8 described below.

Depiction of the virtual needle image 640 of the needle 110 as described above is performed in the present embodiment by overlaying the needle image on the ultrasound image 610 of the monitor 150 of FIG. 1. Suitable algorithms of the system 100 as executed by the processor 205 or other suitable component further enable the projected path 650 and the target 660 to be determined and depicted on the monitor 150 atop the ultrasound image 610 of the target 660. The above prediction, detection, comparison, and depiction process is iteratively performed to continue tracking the movement of the needle 110 in real-time.

Enhanced Guidance System with AI-Based Feedback

Figure 7:
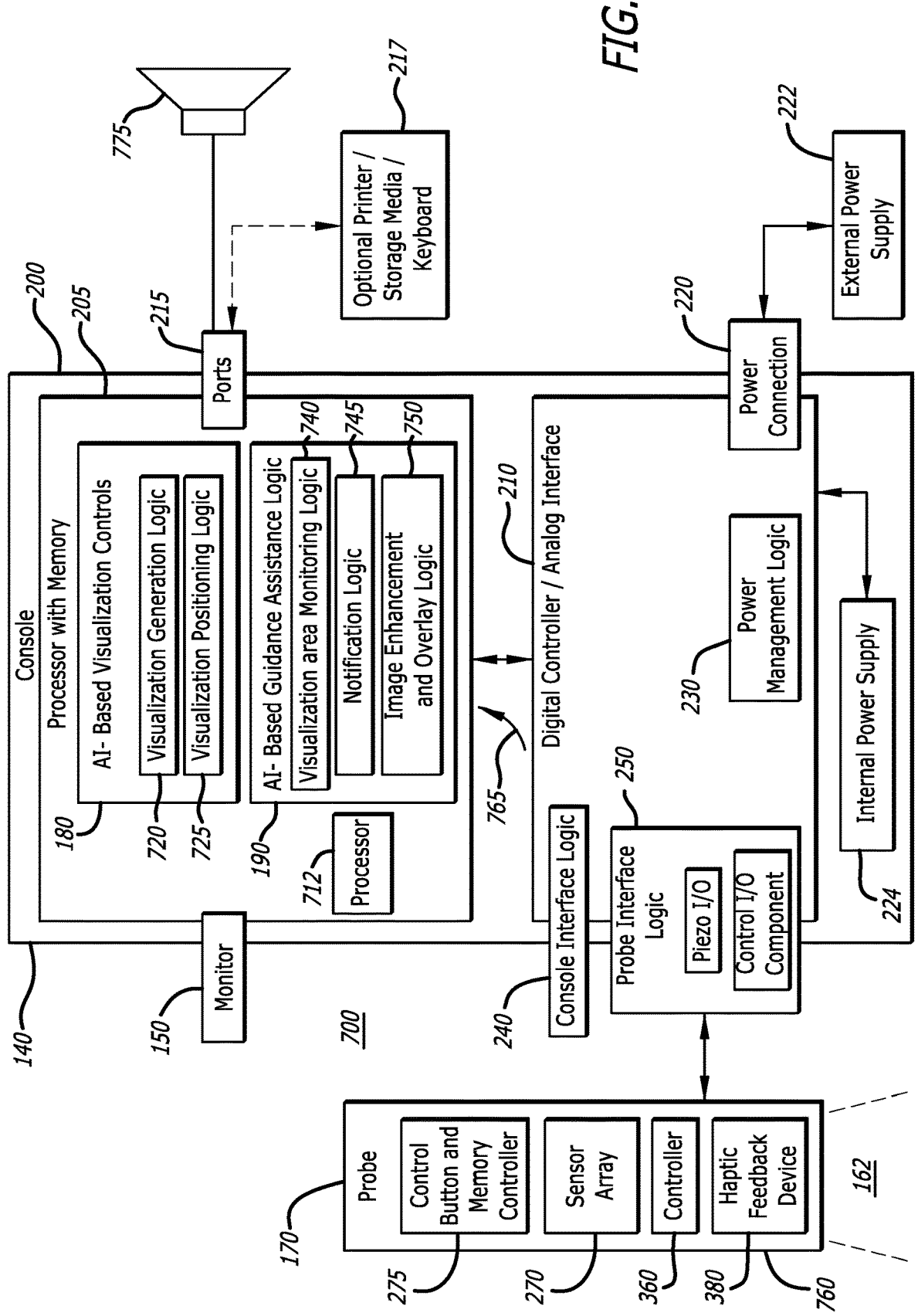
FIG. 7 is an exemplary embodiment of the architecture of the AI-based guidance system of FIG. 1, according to a second embodiment of the guidance system.

Referring to FIG. 7, an exemplary embodiment of the architecture of the guidance system 100 of FIG. 1 with the AI-based visualization controls 180 and the AI-based guidance assistance logic 190 (hereinafter, "AI-based guidance system 700") is shown. Herein, the AI-based guidance system 700 features the console 140, the monitor 150 and the probe 160 as illustrated in FIGS. 1-3. More specifically, according to this embodiment, the console 140 features one or more sets of components within its housing 710, which may be oriented in a variety of forms.

Similar to the embodiment illustrated in FIG. 1 and described above, the AI-based guidance system 100 may include a first set of components such as one or more ports 215 for connection with additional components such as optional components 217 (e.g., printer, storage media, keyboard, etc.). The ports 215, according to one embodiment of the disclosure, may include USB ports, although other port types or a combination of port types can be used. The power connection 220 is included with the console 140 to enable operable connection to the external power supply 222. The internal power supply (e.g., battery) 224 can also be employed either with or exclusive from the external power supply 222.

As a second set of components, the AI-based guidance system 700 may further include console interface logic 240 and/or probe interface logic 250, which may be included on the probe 160 and may be deployed within the console 140 itself. The console interface logic 240 enables a clinician to alter operability of the console 140 via a physical interface. The probe interface logic 250 allows a clinician with control in selecting a desired mode to the monitor 150 for assisting in the needle placement procedure, as described above. Signaling from the probe 160 are routed to the console 140 via the probe interface logic 250. The probe interface 250 includes the piezo I/O component 260 operating as an interface for the sensor array 270 and the control I/O component 265 operating as an interface for the control button and memory controller 275.

A third set of components within the console 140 may include the digital controller/analog interface 210, which communicates with both the processor 205 and other system components that govern the interfacing between the probe 160 as well as other system components. As shown in FIG. 7, the digital controller/analog interface 210 includes the power management logic 230 regulates power use and distribution within the console 140.

A fourth set of components may include the processor with memory 205, namely a processor 712 with access to logic within a memory 715, such as a non-volatile memory (e.g., electrically erasable programmable read only memory (flash), battery-backed random access memory, etc.) for example. The processor 712 is configured to control functionality of the AI-based guidance system 700, thus acting as a control processor. The memory 715 features the AI-based visualization controls 180 and the AI-based guidance assistance logic 190. In particular, the AI-based visualization controls 180 include visualization area generating logic 720 and visualization area positioning logic 725. The AI-based guidance assistance logic 190 includes visualization area monitoring logic 740, notification logic 745 and image enhancement and overlay logic 750, where the operability of these logics 740-750 is described below.

More specifically, upon execution by the processor 712, the visualization area generation logic 720 and the visualization area positioning logic 725 of the AI-based visualization controls 180 are configured to generate and reposition, as needed, a sub-region (visualization area 195) of the total imaging area captured by the ultrasound beam 162 based on information received from the medical component tracking subsystem (e.g., sensor array 270 and piezo I/O component 260).

In particular, the probe 160 is employed in connection with ultrasound-based visualization of a vasculature, such as a vein or artery for example, in preparation for insertion of the medical component 110 (e.g., needle, catheter, etc.) into the vasculature 120. Such visualization gives real time ultrasound guidance and assists in reducing complications typically associated with such introduction. As shown, according to one embodiment of the disclosure, the probe 160 includes a housing 760 that features the button/memory controller interface 275, the sensor array 270, which includes the piezoelectric array 340, the controller 360 and/or the haptic feedback device 380, where the operations of the same are described above.

Herein, the processor 712 is configured to receive an image of a region of the patient (e.g., skin surface and the subcutaneous tissue) captured by the ultrasound beam 162 emitted from the probe 160. Additionally, the AI-based visualization controls 180 are configured to receive orientation metrics 765 of the needle 110 from the probe 160, and based on these orientation metrics 765, the visualization area generation logic 720, when executed by the processor 712, generates the visualization area 195, which may correspond to a portion of the total imaging area 192 rendered by the guidance system 100 (see FIGS. 8A-8E). For this embodiment, the visualization area is substantially lesser in size (e.g., less than a $1/10^{th}$ of size) than the total imaging area in order to (i) reduce complexity in analysis of the visualization area by the visualization area monitoring logic 740 (in determining a presence of the needle upon detecting needle reflection) and (ii) reduce the latency in reporting the analysis results. The sizing of the visualization area may be static or dynamic (e.g., based on needle gauge, medical component type, etc.).

Also, based on the orientation metrics 765, the visualization area positioning logic 725, when executed by the processor 712, may alter the location of the visualization area based, at least in part on, the position, orientation and the current path of advancement of the needle 110. More specifically, the visualization area positioning logic 725 may alter the location of the visualization area in order to intercept advancement of the needle 110 prior to contact with an outer wall surface of the targeted vasculature 120.

The visualization area monitoring logic 740, when executed by the processor 712, is configured to monitor the visualization area for needle reflection, namely artifacts that identify the needle 110 has entered into and/or exited from the visualization area 195. Upon detecting the needle 110 entering the visualization area, the visualization area monitoring logic 740 signals the notification logic 745 to initiate a visual notification to the monitor 150 upon detection of the needle crossing into or existing the visualization area. Additionally, or in the alterative, the notification logic 745 may be configured to initiate an audible notification to the audio device (e.g., speaker) 775 associated with the monitor 150 or a haptic notification directed to the haptic feedback device 380 of the probe 160 upon detection of the needle crossing into or existing the visualization area.

The audio/visual/tactile notification logic 745 may include hardware and/or software that signals an associated device (e.g., a monitor, computer, audio device, and/or other display) to provide the user with an audio, visual, and/or tactile indication/notification of the proximity of the medical component (needle) 110 to the predetermined location. The audio, visual, and/or tactile notification may take a variety of forms, including as a graphical or numerical display, a graphical or numerical display of distance between the needle 110 and the vasculature, a graphical representation of the needle 110 moving relative to a graphical representation of the vasculature, a sound (e.g., a beep) that changes frequency depending on the location of the needle 110 relative to the desired location, display colors may change depending on the location of the needle (e.g., a red color may be displayed if the tip is incorrectly positioned), a vibration of one or more of the components of the system (e.g., haptic feedback), a change in temperature of one or more of the components of the system, etc., and combinations thereof.

The image enhancement and overlay logic 750 is configured to overlay the visualization area over the ultrasonically captured an image of a targeted vasculature. Additionally, the logic 750 may be configured to determine the image associated with the needle 110 and apply imaging enhancements to the needle image to better identify the presence, location and/or orientation of the needle.

Referring to FIGS. 8A-8E, exemplary embodiments of an embodiment of the visualization area that is generated and monitored by the AI-based guidance system of FIG. 7 for a presence of needle reflection within the visualization area 195, which triggers enhanced display of a medical component (e.g., needle) and audio/visual/tactile notification.

As shown in FIG. 8A, a first screenshot 800 of an ultrasound image (or series of ultrasound images) captured by the sensor array located within the probe and rendered on the monitor 150 is shown. Herein, the first screenshot 800 illustrates the needle 110 advancing through subcutaneous tissue 805 toward the vasculature 120. Generated by the visualization area generation logic 720 of FIG. 7, the visualization area 195 is superimposed, in real-time, over an ultrasound image 810 that displays the targeted vasculature 120 and the subcutaneous tissue 805 surrounding the vasculature 120. Represented as a dashed box, the visualization area 195 defines an area within which needle reflection is monitored.

Furthermore, for this embodiment, the AI-based guidance system tracks the positioning and advancement of the needle 110 in accordance with numerous degrees of motion as illustrated by a second screenshot 820 in FIG. 8B. Herein, the position of the visualization area 195 is adjusted to accommodate an angular adjustment 825 of the needle 110. The re-positioning is determined from the orientation metrics that corresponds or is related to the xyz spatial coordinate space, pitch, and/or yaw (e.g., orientation) of the needle 110.

Such tracking of the needle 110 and re-positioning of the visualization area 195 enables the distal end 112 of the needle 110 to be guided and placed to intersect a border 840 of the visualization area 195, as shown by a third screenshot 830 of FIG. 8C. Upon detecting entry of the distal end 112 of the needle 110 into the visualization area 195 (e.g., based on detected needle reflection associated with the distal end 112), the visualization area monitoring logic 740 (see FIG. 7) signals the notification logic 745 to supply a notification (e.g., signaling associated with visual notification, audible notification, haptic notification or any combination thereof) to a device associated with the console 140 (e.g., monitor 150, speaker 155, probe 160).

Figure 8D:
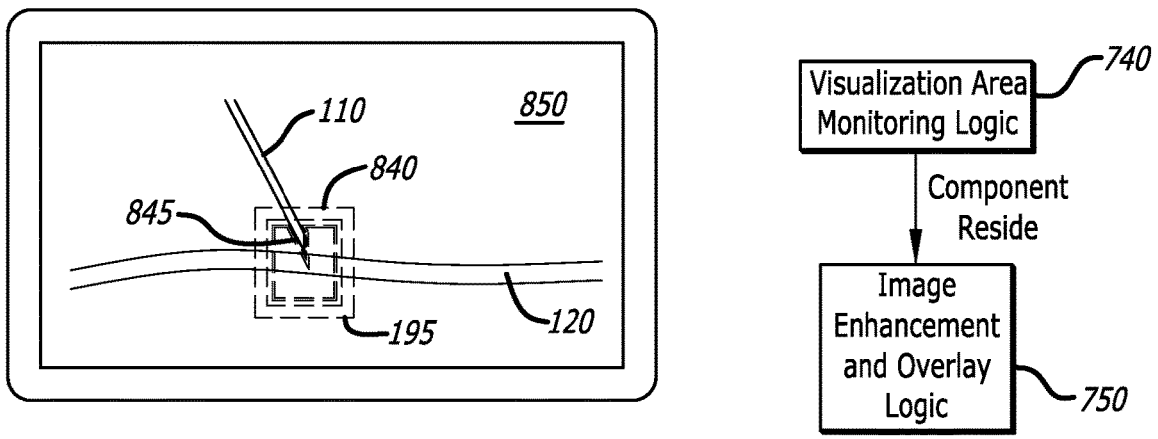

Additionally, upon detecting needle reflection within the visualization area 195 by the visualization area monitoring logic 740 of FIG. 7, the image enhancement and overlay logic 750 applies one or more imaging enhancements 845 to items within or forming the visualization area 195 such as the needle 110, the border 840 of the visualization area 195 or the like, as shown in a fourth screenshot 850 in FIG. 8D. The imaging enhancements may include, but are not limited or restricted to altering the displayed image of the needle (e.g., change color, highlight, lighten or darker from the rest of the ultrasound image, etc.), altering the resolution of the visualization area 195 by generating a higher resolution virtualization that corresponds to the visualization area, or the like.

Figure 8E:
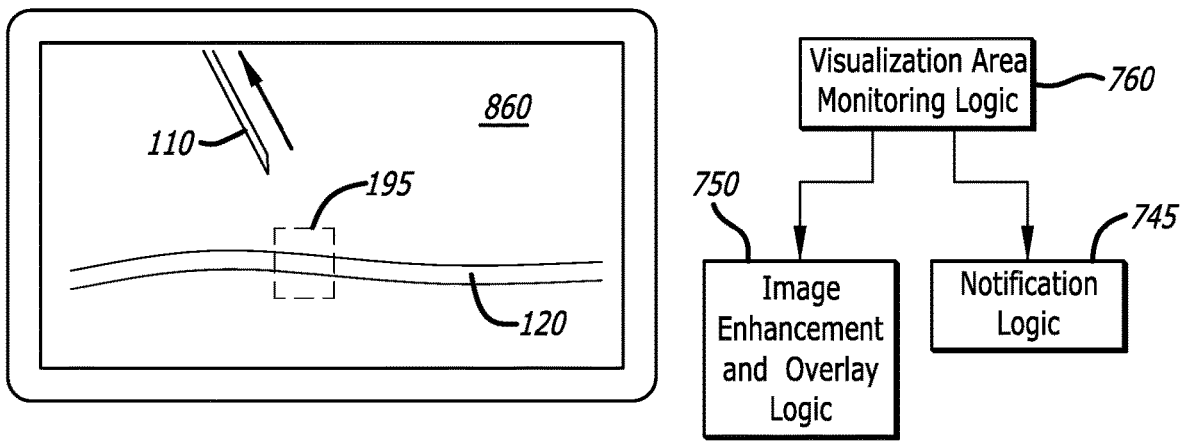

As now shown in a fifth screenshot 860 of FIG. 8E, upon removal of the needle 110 from the visualization area 195, the visualization area monitoring logic 740 signals the AI-based image enhancement and overlay logic 750 to cease generation of the imaging enhancements. Optionally, upon removal of the needle 110 from the visualization area 195, the visualization area monitoring logic 740 signals the AI-based notification logic 745 to generate a notification (visual, audible, and/or haptic) to notify the clinician that the needle 110 has exited the visualization area 195.

Figure 9A:
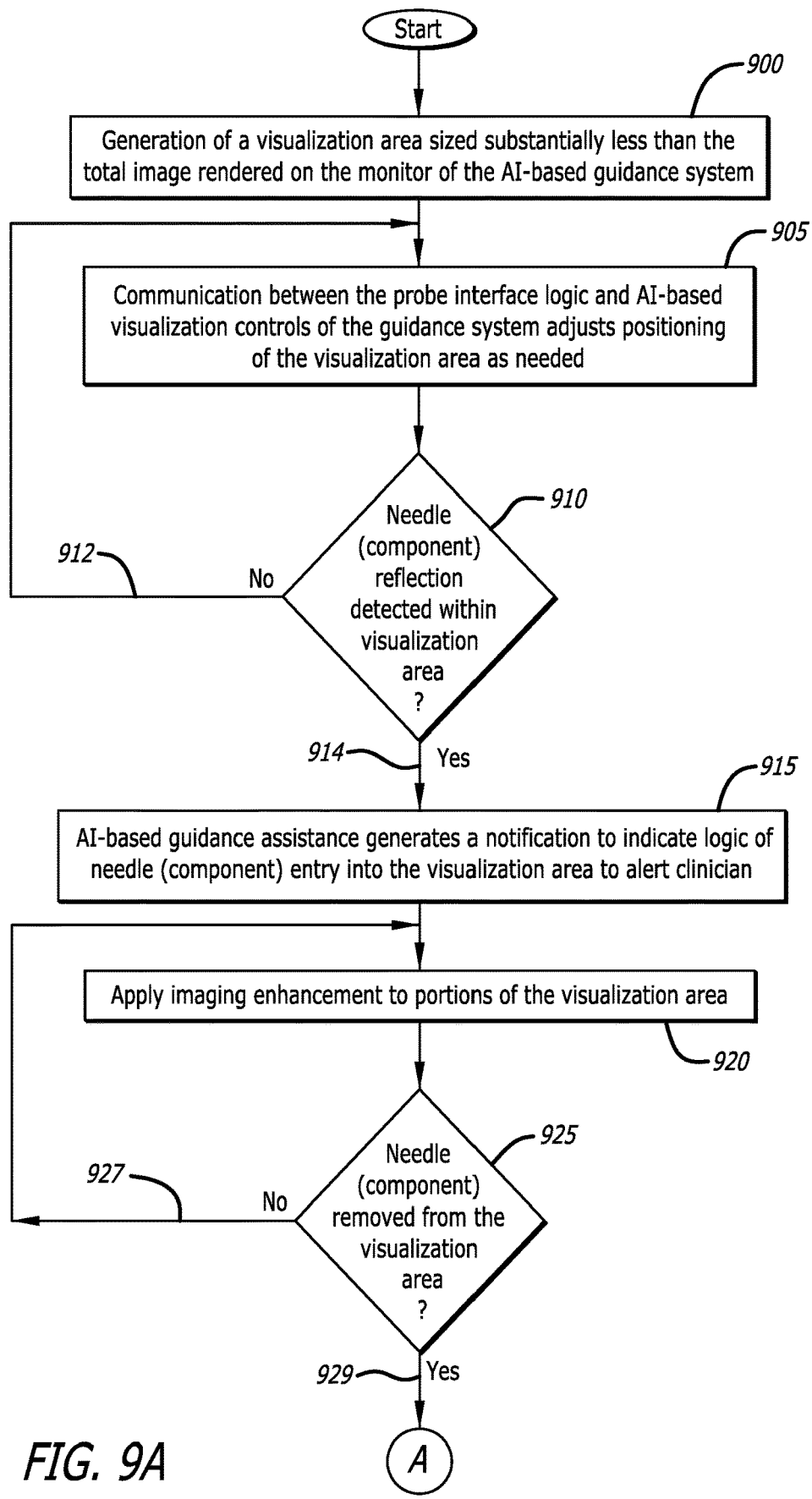
FIGS. 9A-9B are an exemplary embodiment of a method of operation conducted by the AI-based guidance assistance logic of FIG. 7.
Figure 9B:
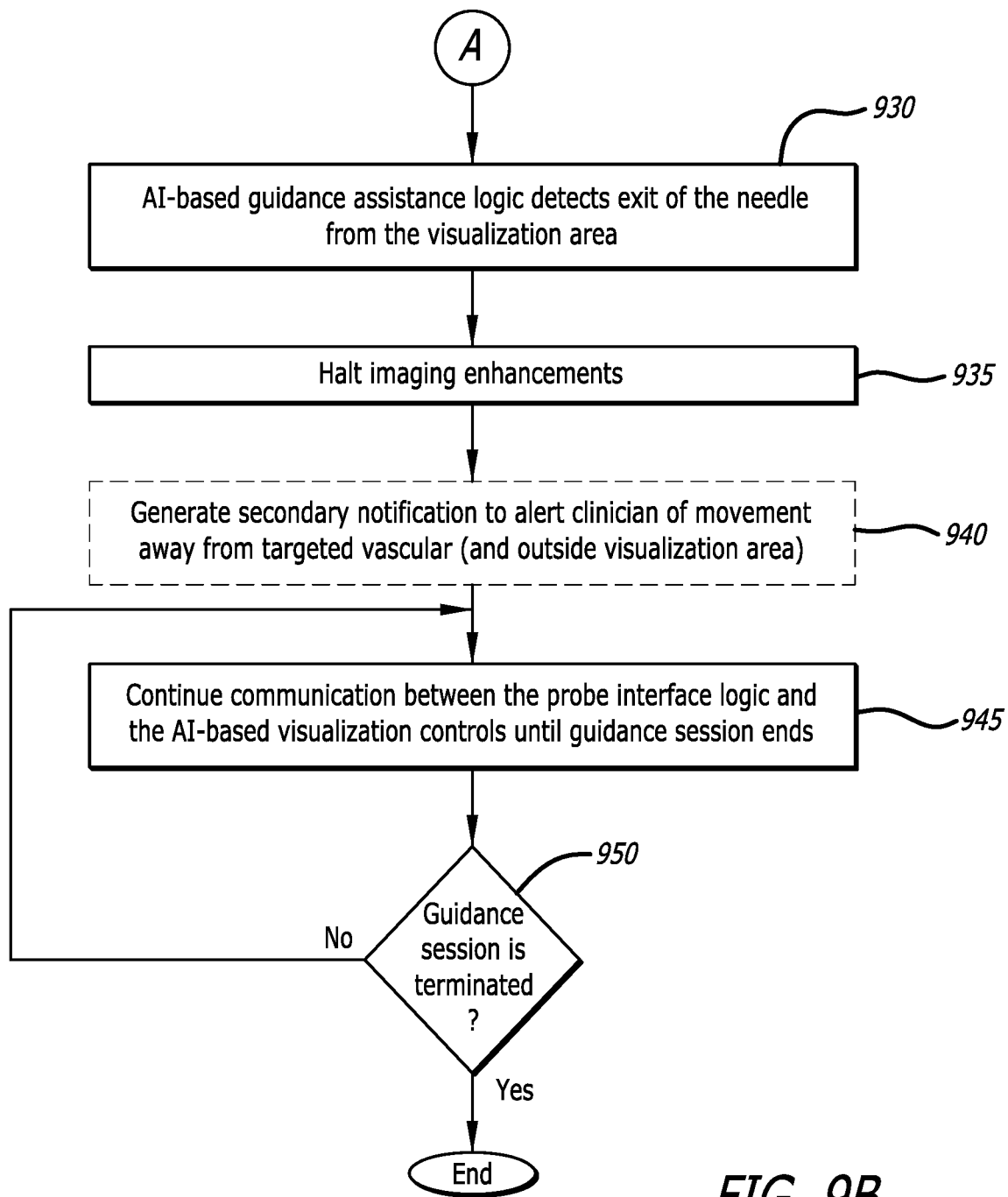

Referring now to FIG. 9A-9B, an exemplary embodiment of a method of operation conducted by the AI-based guidance assistance logic of FIG. 7 is shown. Herein, as shown in FIG. 9A, the visualization area, sized substantially less than the total imaging area, is generated and rendered on the monitor of the AI-based guidance system (operation 900). According to one embodiment, the visualization area overlays a portion of the total imaging area proximate to a targeted vasculature. Thereafter, based on communications between the probe interface logic and the AI-based visualization controls, the positioning of the visualization area is adjusted. The adjustment is made by the AI-based visualization controls to position the visualization area around the vasculature so as to intercept the advancement of a medical component (e.g., needle) directed to that vasculature (operation 905).

In response to failing to detect needle reflection, the AI-based guidance assistance logic continues to monitor for artifacts (e.g., needle reflection, etc.) that identify a presence of the needle within the visualization area (operations 910, 912). However, upon detecting needle reflection, the AI-based guidance assistance logic identifies entry of the needle into the visualization area and generates a notification to alert a clinician of the positioning of the needle (operations 914, 915). Certain images within the visualization area are selected to undergo imaging enhancements by the AI-based guidance assistance logic, such as altering the displayed appearance of the needle (e.g., change in color, highlight, or outline for example (operation 920). The imaging enhancements continue while the needle is within the visualization area (operations 925, 927).

Responsive to the needle being removed from the visualization area as detected by the AI-based guidance assistance logic, as shown in FIG. 9B, the imaging enhancements are halted (operations 929, 930, 935). Optionally, the AI-based guidance assistance logic may generate a secondary notification to alert the clinician of movement of the needle away from the targeted vasculature (operation 940). Communications between the probe interface logic and the AI-based visualization controls continue (in case of a secondary needle insertion, etc.) until the guidance session (ultrasound session) is terminated (operations 945, 950).

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A guidance system, comprising:
   a probe configured to obtain an ultrasound image; and
   a console communicatively coupled to the probe, the console comprising a processor and non-transitory, computer-readable medium having stored thereon logic, that when executed by the processor, causes performance of operations including:
      determining positioning of a visualization area within the ultrasound image, wherein the visualization area corresponds to a portion of a targeted vasculature at which a needle is expected to contact, wherein the needle is associated with a magnetic element from which a magnetic field is detected by the probe,
      generating a display of the ultrasound image and the visualization area on a display screen, wherein a border is superimposed on the ultrasound image surrounding the visualization area,
      monitoring for a presence of the needle within a patient body corresponding to the visualization area based on position and orientation information of the needle derived from the magnetic field, and
      in response to detection of the presence of the needle within an area of the patient body corresponding to the visualization area, generating and applying an imaging enhancement visualization to at least a portion of imaged data within the visualization area being an alteration of a visual style of the border of the visualization area based on entry into the area of the patient body corresponding to the visualization area, wherein the imaging enhancement visualization is configured to assist in advancement of the needle toward the targeted vasculature, and wherein the visualization area is a sub-region of a total imaging area rendered by the console.

2. The guidance system as defined in claim 1, wherein the operations further include:
   monitoring for needle feedback from sound waves emitted and recovered by the probe.

3. The guidance system as defined in claim 1, wherein the needle from which a needle reflection is detected when the probe is operating as a part of an ultrasound system.

4. The guidance system as defined in claim 1, wherein the operations further include:
monitoring for needle feedback based on the magnetic field detected by the probe based on the magnetic element being deployed within the needle.

5. The guidance system as defined in claim 1, wherein the operations further include:
generating feedback that visibly identifies the presence of the needle within the visualization area.

6. The guidance system as defined in claim 5, wherein the operations further include:
generating signaling to illuminate a light element within the probe that identifies the needle is within the visualization area proximate to the targeted vasculature.

7. The guidance system as defined in claim 1, wherein the operations further include:
generating feedback to an audio device for use in generating an audible notification to identify the presence of the needle within the visualization area proximate to the targeted vasculature.

8. The guidance system as defined in claim 1, wherein the operations further include:
generating feedback to a haptic feedback device deployed within the probe for use in generating a haptic notification operating as a controlled of the probe.

9. The guidance system as defined in claim 1, wherein the console further comprises artificial intelligence based (AI-based) visualization controls to generate the visualization area and AI-based guidance assistance logic to (i) monitor for the presence of the needle within the visualization area proximate to the targeted vasculature, (ii) provide feedback to a device for generating the notification of the presence of the needle within the visualization area, and (iii) generate and apply an imaging enhancement to at least the portion of the imaged data within the visualization area to assist in an advancement of the needle toward the targeted vasculature.

10. The guidance system as defined in claim 1, wherein the imaging enhancement visualization includes a color overlay of at least a portion of an image of the needle to provide better clarity as to a position of the needle.

11. The guidance system as defined in claim 1, wherein the imaging enhancement visualization includes a virtual representation of the visualization area with the needle and the targeted vasculature.

12. The guidance system as defined in claim 9, wherein the notification includes an activation of a light on the probe or a light of the console to identify whether the needle is entering or exiting the targeted vasculature.

13. A guidance system for assisting in an advancement of a needle within a body of a patient, comprising:
a probe configured to obtain an ultrasound image; and
a console including a processor and memory, wherein the console is communicatively coupled to the probe, the memory having stored thereon logic that, when executed by the processor, is configured to cause performance of operations including:
determining positioning of a visualization area within the ultrasound image, wherein the visualization area corresponds to a subset of the ultrasound image and corresponds to a portion of a targeted vasculature at which the needle is expected to contact based on a position and an orientation of the needle, wherein the needle is associated with a magnetic element from which a magnetic field is detected by the probe;
generating a display of the ultrasound image and the visualization area on a display screen, wherein a border is superimposed on the ultrasound image surrounding the visualization area;
monitoring for a presence of the needle within the body of the patient corresponding to the visualization area based on position and orientation information of the needle derived from the magnetic field; and
in response to detection of the presence of the needle within an area of the body of the patient corresponding to the visualization area, generating and applying an imaging enhancement visualization to at least a portion of imaged data within the visualization area being an alteration of a visual style of the border of the visualization area based on entry into the area of the body of the patient corresponding to the visualization area, wherein the imaging enhancement visualization is configured to assist in the advancement of the needle toward the targeted vasculature, and wherein the visualization area is a sub-region of a total imaging area rendered by the console.

14. The guidance system as defined in claim 13, wherein the operations further include:
generating the visualization area to overlay a portion of the total imaging area rendered by the guidance system; and
positioning and re-positioning the visualization area within the total imaging area along a path to intercept the visualization area.

15. The guidance system as defined in claim 13, wherein the imaging enhancement visualization includes a color overlay of at least a portion of an image of the needle to provide better clarity as to the position of the needle.

16. The guidance system as defined in claim 13, wherein the operations further include:
activating a light on the probe or a light of the console to identify whether the needle is entering or exiting the targeted vasculature.

17. The guidance system as defined in claim 13, wherein a needle reflection is detected from return sound waves generated by the probe when the console is operating as a part of an ultrasound system.

18. The guidance system as defined in claim 13, wherein the operations further include:
providing a feedback to a device for generating a notification of the presence of the needle within the visualization area.

19. The guidance system as defined in claim 13, wherein the magnetic element is disposed within a hub coupled to the needle.

20. A method comprising:
obtaining an ultrasound image from an ultrasound probe;
determining a visualization area being a portion of the ultrasound image, wherein the visualization area corresponds to a subset of the ultrasound image and corresponds to a portion of a targeted vasculature at which a needle is expected to contact based on a position and an orientation of the needle, wherein the needle is associated with a magnetic element from which a magnetic field is detected by the ultrasound probe;
generating a display of the ultrasound image and the visualization area on a display screen, wherein a border is superimposed on the ultrasound image surrounding the visualization area;
monitoring for a presence of the needle within a patient body corresponding to the visualization area based on position and orientation information of the needle derived from the magnetic field; and in response to detection of the presence of the needle within an area of the patient body corresponding to the visualization area, generating and applying an imaging enhancement visualization to at least a portion of imaged data within the visualization area being an alteration of a visual style of the border of the visualization area based on entry into the area of the patient body corresponding to the visualization area, wherein the imaging enhancement visualization is configured to assist in advancement of the needle toward the targeted vasculature, and wherein the visualization area is a sub-region of a total imaging area rendered by a console.

21. A guidance system for assisting in an advancement of a needle within a body of a patient, comprising:

a probe configured to obtain an ultrasound image; and a console including a processor and memory, wherein the console is communicatively coupled to the probe, the memory having stored thereon logic that, when executed by the processor, is configured to cause performance of operations including:

determining positioning of a visualization area within the ultrasound image, wherein the visualization area corresponds to a subset of the ultrasound image and corresponds to a portion of a targeted vasculature at which the needle is expected to contact based on a position and an orientation of the needle;

activating a light on the probe or a light of the console that identifies whether the needle is entering or exiting the targeted vasculature;

generating a display of the ultrasound image and the visualization area on a display screen, wherein a border is superimposed on the ultrasound image surrounding the visualization area;

monitoring for a presence of the needle within the body of the patient corresponding to the visualization area based on position and orientation information of the needle derived from a magnetic field; and in response to detection of the presence of the needle within an area of the body of the patient corresponding to the visualization area, generating and applying an imaging enhancement visualization to at least a portion of imaged data within the visualization area being an alteration of a visual style of the border of the visualization area based on entry into the area of the body of the patient corresponding to the visualization area, wherein the imaging enhancement visualization is configured to assist in the advancement of the needle toward the targeted vasculature, and wherein the visualization area is a sub-region of a total imaging area rendered by the console.

* * * * *